United States Patent
Eckhardt et al.

(10) Patent No.: US 6,387,625 B1
(45) Date of Patent: May 14, 2002

(54) MONOLAYER AND ELECTRODE FOR DETECTING A LABEL-BEARING TARGET AND METHOD OF USE THEREOF

(75) Inventors: Allen E. Eckhardt, Durham; Jill C. Mikulecky, Creedmoor; Mary E. Napier, Carrboro; Robert S. Thomas, Efland; H. Holden Thorp, Chapel Hill, all of NC (US)

(73) Assignees: The University of North Carolina at Chapel Hill, Chapel Hill, NC (US); Xanthon, Inc., Research Triangle Park, NC (US)

( * ) Notice: Subject to any disclaimer, the term of this patent is extended or adjusted under 35 U.S.C. 154(b) by 0 days.

(21) Appl. No.: 09/596,607

(22) Filed: Jun. 19, 2000

Related U.S. Application Data

(63) Continuation-in-part of application No. 09/179,665, filed on Oct. 27, 1997, now Pat. No. 6,132,971, which is a division of application No. 08/667,338, filed on Jun. 20, 1996, now Pat. No. 5,871,918, which is a continuation-in-part of application No. 08/495,817, filed on Jun. 27, 1995, now abandoned, which is a continuation-in-part of application No. 08/950,503, filed on Oct. 14, 1997, now Pat. No. 5,968,745, which is a continuation-in-part of application No. 08/667,338, filed on Jun. 20, 1996, now Pat. No. 5,871,918.

(51) Int. Cl.[7] .......................... C12Q 1/68; C12M 1/34; G01R 27/08; G01N 33/00; C07H 21/02
(52) U.S. Cl. .......................... 435/6; 435/288; 435/291; 435/810; 204/153.12; 324/715; 436/94; 536/23.1
(58) Field of Search ..................... 204/153.12; 324/715; 435/6, 288, 291, 810, 817; 436/94, 501; 536/23.1, 24.3

(56) References Cited

U.S. PATENT DOCUMENTS

| | | | |
|---|---|---|---|
| 4,545,382 A | 10/1985 | Higgins et al. | 128/635 |
| 4,683,195 A | 7/1987 | Mullins et al. | 435/6 |
| 4,704,353 A | 11/1987 | Humphries et al. | 435/4 |

(List continued on next page.)

FOREIGN PATENT DOCUMENTS

| | | | |
|---|---|---|---|
| EP | 0 478 319 A1 | 4/1992 | C12Q/1/68 |
| EP | 0 478 319 A1 | 6/1992 | C12Q/1/68 |
| EP | 0 587 408 A1 | 3/1994 | C12Q/1/00 |
| EP | 0 402 917 B1 | 11/1996 | G01N/33/48 |
| JP | 3076600 | 4/1991 | |
| WO | WO 85/02627 | 6/1985 | |
| WO | WO 91/15768 | 10/1991 | |
| WO | WO 93/20230 | 10/1993 | |
| WO | WO 94/22889 | 10/1994 | |
| WO | WO 95/00530 | 1/1995 | |
| WO | WO 97/02359 | 1/1997 | |
| WO | WO 97/44651 | 11/1997 | |
| WO | WO 98/20162 | 5/1998 | |
| WO | WO 98/23948 | 6/1998 | |

OTHER PUBLICATIONS

The Chip of the 90s, *Chemistry in Britain*, pgs 122–125 (Feb. 1995).
Carter et al.; Voltammetric Studies of the Interaction of Metal Chelates with DNA. 2. Tris–Chelated Complexes of Cobalt(III) and Iron(II) with 1,10–Phenanthroline and 2, 2'–Bipyridine, *J. Am. Chem. Soc.*, 111(24):8901–8911 (1989).
Chee et al.; Accessing Genetic Information High–Density DNA Arrays, *Science*, 274:610–614 (1996).
Daube et al.; Typing of Clostridium Perfringens byIn Vitro Amplification of Toxin Genes, *Journal of Applied Bacteriology*, 77:650–655 (1994).
Du et al.; [10]Automated Fluorescent DNA Sequencing of Polymerase Chain Reaction Products, *Methods in Enzymology*, 218:104–121 (1993).
Fedorova et al.; Application of Tris(2,2'–Bipyridyl)Ruthenium(III) for the Investigation of dNA Spatial Structure by A Chemical Modification Method, *J. of Inorganic Biochemistry*, 34:149–155 (1988).
Fodor et al., Multiplexed BiochemicalAassays with Biological Chips, *Product Review*, 364:555–556 (Aug. 5, 1993).
Fodor et al.; Light–Directed, Spatially Addressable Parallel Chemical Synthesis, *Research Article*, 767–773 (Feb. 15, 1991).
Guatelli et al.; Isothermal, in vitro Amplification of Nucleic Acids by a Multienzyme Reaction Modeled After Retroviral Replication, *Proc. Natl. Acad. Sci.*, 87:1874–1878 (1990).
Hall et al.; An Electrochemical Method for Detection of Nucleic Acid Hybridisation, *Biochemistry and Molecular Biology International*, 32(1):21–28 (1994).
Holodniy et al.; Determination of Human Immunodeficiency Virus RNA in Plasma and Cellular Viral DNA Genotypic Zidovudine Resistance and Viral Load During Zidovudine–Didanosine Combination Therapy, *J. of Viroloagy*, 69(6):3510–3516 (1995).
Jenkins et al.; A Sequence–Specific Molecular Light Switch: Tethering of an Oligonucleotide to a Dipyridophenazine Complex of Ruthenium(II), *J. Am. Chem. Soc.*, 114:8736–8738 (1992).

(List continued on next page.)

*Primary Examiner*—Jeffrey Fredman
*Assistant Examiner*—Arun K. Chakrabarti
(74) *Attorney, Agent, or Firm*—Myers Bigel Sibley & Sajovec

(57) ABSTRACT

An electrode for detecting interactions between members of a binding pair, which electrode has been modified by formation of a non-conductive self-assembled monolayer, and a method of detecting biomolecules, such as nucleic acids or other targets, including receptors, ligands, antigens or antibodies, utilizing such an electrode. When contacted with a target nucleic acid, an oligonucleotide probe coupled to the self-assembled monolayer reacts with the target nucleic acid form a hybridized nucleic acid on the modified electrode surface. The hybridized nucleic acid is reacted with a transition metal complex capable of oxidizing a preselected base in the hybridized nucleic acid in an oxidation-reduction reaction, the oxidation-reduction reaction is detected, and the presence or absence of the nucleic acid is determined from the detected oxidation-reduction reaction.

23 Claims, 6 Drawing Sheets

U.S. PATENT DOCUMENTS

| | | | | |
|---|---|---|---|---|
| 4,800,159 | A | | 1/1989 | Mullis et al. ............ 435/172.3 |
| 4,840,893 | A | * | 6/1989 | Hill et al. ....................... 435/6 |
| 4,883,579 | A | | 11/1989 | Humphries et al. ......... 204/403 |
| 4,908,307 | A | | 3/1990 | Rodland et al. ................ 435/6 |
| 4,945,045 | A | | 7/1990 | Forrest et al. ................. 435/25 |
| 4,963,815 | A | * | 10/1990 | Hafeman ..................... 324/715 |
| 4,965,188 | A | | 10/1990 | Mullis et al. ................... 435/6 |
| B14,683,202 | A | | 11/1990 | Mullins ........................ 435/91 |
| 5,066,372 | A | | 11/1991 | Weetall ................... 204/153.1 |
| 5,108,889 | A | | 4/1992 | Smith ............................ 435/4 |
| 5,112,974 | A | | 5/1992 | Barton .......................... 546/4 |
| 5,143,854 | A | | 9/1992 | Pirrung et al. .............. 436/518 |
| 5,157,032 | A | | 10/1992 | Barton ....................... 514/185 |
| 5,171,853 | A | | 12/1992 | Thorp et al. .................. 536/27 |
| 5,175,082 | A | | 12/1992 | Jeffreys ......................... 435/6 |
| 5,194,372 | A | | 3/1993 | Nagai et al. .................... 435/6 |
| 5,272,056 | A | | 12/1993 | Burrows ........................ 435/6 |
| 5,278,043 | A | * | 1/1994 | Bannwarth et al. ........ 536/23.1 |
| 5,312,527 | A | * | 5/1994 | Mikkelsen et al. ..... 204/153.12 |
| 5,378,628 | A | | 1/1995 | Gratzel et al. .............. 435/288 |
| 5,405,783 | A | | 4/1995 | Pirrung et al. .............. 436/518 |
| 5,439,829 | A | | 8/1995 | Anderson et al. ........... 436/518 |
| 5,532,129 | A | | 7/1996 | Heller ........................... 435/6 |
| 5,565,322 | A | | 10/1996 | Heller ........................... 435/6 |
| 5,605,662 | A | | 2/1997 | Heller et al. ............... 422/68.1 |
| 5,632,957 | A | | 5/1997 | Heller et al. ............... 422/68.1 |
| 5,667,976 | A | | 9/1997 | Van Ness et al. ............... 435/6 |
| 5,688,642 | A | | 11/1997 | Chrisey et al. ................ 435/6 |
| 5,711,868 | A | | 1/1998 | Maley et al. ............ 205/782.5 |
| 5,776,672 | A | | 7/1998 | Hashimoto et al. ............ 435/6 |
| 6,180,352 | B1 | * | 1/2001 | Meade et al. ................... 435/6 |

OTHER PUBLICATIONS

Johnston et al.; Trans–Dioxorhenium(V)–Mediated Electrocatalytic Oxidation of DNA at Indium Tin–Oxide Electrodes: Voltammetric Detection of DNA Cleavage in Solution, *Inorg. Chem.*, 33(26):6388–6390 (1994).

Johnston et al.; Electrochemical Measurement of the Solvent Accessibility of Nucleobases Using Electron Transfer between DNA and Metal Complexes, *J. Am. Chem. Soc.*, 117(35):8933–3938 (1995).

Kwoh et al.; Target Amplification Systems in Nucleic Acid–Based Diagnostic Approaches, pp. 14–25, Oct. 1990.

Kwoh et al.,; Transcription–Based Amplication System and Detection of Amplified Human Immunodeficiency Virus Type 1 with a Bead–Based Sandwich Hybridization Format, *Proc. Natl. Acad. Sci.*, 86:1173–1177 (1989).

Lewis, PCR's Competitors Are Alive and Well and Moving Rapidly Towards Commercialization, *Genetic Engineering News*, 3 pages (1992).

Lishanski et al.; Mutation Detection by Mismatch Binding Protein, MutS, in Amplified DNA: Application to the Cystic Fibrosis Gene, *Proc. Natl. Acad. Sci.*, 91:2674–2678 (1994).

Lizardi et al.; Exponential Amplification of Recombinant–RNA Hybridization Probes, *Bio/Technology*, 6:1197–1202 (1998).

Lulitanond et al.; Detection of Herpes Simplex Virus Type 2 Bgl II N Fragment in Paraffin–Embedded Cervical Tissue Sections Using Nested Polymerase Chain Reaction, *Molecular and Cellular Probes*, 8:441–447 (1994).

Maeder et al.; Nonlinear Least–Squares Fitting of Multivariate Absorption Data, *Anal. Chem.*, 62(20):2220–2224 (1990).

Maher III; Inhibition of T7 RNA Polymerase Initiation by Triple–Helical DNA Complexes: A Model for Artificial Gene Repression, *Biochemistry*, 31(33):7587–7594 (1992).

Marchand–Brynaert et al.; Surface Functionalization of Poly(ethylene terephthalate) Film and Membrane by Controlled Wet Chemistry: Chemical Characterization of Carboxylated Surfaces, *J. of Colloid and Interface Science*, 173:236–244 (1995).

W. John Martin; 33 Infectious Diseases, *The Polymerase Chain Reaction (K.B. Mullis, F. Ferré, R.A. Gibbs, Editors, © 1994 Birkhauser Boston )*, 406–417.

Meade et al.; Electron Transfer through DNA: Site–Specific Modification of Duplex DNA with Ruthenium Donors and Acceptors, *Angew. Chem. Int. Ed. Engl.* , 34(3):352–354 (1995).

Millan et al.; Sequences–Selective Biosensor for DNA Based on Electroactive Hybridization Indicators, *Anal. Chem.*, 65(17):2317–2323 (1993).

Millan et al.; Voltammetric DNA Biosensor for Cystic Fibrosis Based on a Modified Carbon Paste Electrode, *Anal. Chem.*, 66(18):2943–2948 (1994).

Murphy et al.; Long–Range Photoinduced Transfer Through a DNA Helix, *Science*, 262:1025–1029 (1993).

Murphy et al.; Fast Photoinduced Electron Transfer Through DNA Intercalation, *Proc. Natl. Acad. Sci.* , 91:5315–5319 (1994).

Neubauer et al.; Prognostic Importance of Mutations in the Ras Proto–Oncogenes in De Novo Acute Myeloid Leukemia, *Blood*, 83(6):1603–1611 (1994).

Nielsen et al.; Sequence–Selective Recognition of DNA by Strand Displacement with a Thymine–Substituted Polyamide, *Science*, 254:1497–1500 (1991).

DNA Sequencing on a Chip, Compact Arrays of Probes May be Used for Ultrafast DNA Sequencing if Fabrication and Interpretation Problems Can Be Solved, *Analytical Chemistry*, 67(5):201 A–204A (1995).

Osteryoung; Voltammetry for the Future, *Acc. Chem. Res.* , 26(3):77–83 (1993).

Pyle et al.; Mixed–Ligand Complexes of Ruthenium(II): Factors Governing Binding to DNA, *J. Am. Chem. Soc.* , 111(8):3051–3058 (1989).

Ried et al.; Simultaneous Visualization of Seven Different DNA Probes by in situ Hybridization Using Combinatorial Fluorescence and Digital Imaging Microscopy, *Proc. Natl. Acad. Sci.* , 89:1388–1392 (1992).

Rudolph et al.; A Simulator for Cyclic Voltammetric Responses, *Analytical Chemistry*, 66(10):589 A–600 A (1994).

Saleeba et al.; [19]Chemical Cleavage of Mismatch to Detect Mutations, *Methods in Enzymology*, 217:286–295 (1993).

Satyanarayana et al.; Neither Δ–nor Λ–Tris(Phenanthroline)Ruthenium(II) Binds to DNA by Classical Intercalation, *Biochemistry*, 31(39):9319–9324 (1992).

Schena et al.; Quantitative Monitoring of Gene Express Patterns with a Complementary DNA Microarray, *Science*, 270:467–470 (1995).

Mellors et al.; Prognosis in HIV–1 Infection Predicted by the Quantity of Virus in Plasma, *Science*, 272:1167–1170 (1996).

Spargo et al.; Chemiluminescent Detection of Strand Displacement Amplified DNA from Species Comprising the Mycobacterium Tuberculosis Complex, *Molecular and Cellular Probes*, 7:395–404 (1993).

Steenken et al.; One–Electron–Reduction Potentials of Pyrimidine Bases, Nucleosides, and Nucleotides in Aqueous Solution. Consequences for DNA Redox Chemistry, *J. Am. Chem. Soc.*, 114(12):4701–4709 (1992).

Strobel et al.; Site–Specific Cleavage of a Yeast Chromosome by Oligonucleotide–Directed Triple–Helix Formation, *Science*, pp. 73–75 (Jul. 6, 1990).

Strobel et al.; Minor Groove Recognition of the Conserved G–U Pair at the Tetrahymena Ribozyme Reaction Site, *Science*, 267:675–679 (1995).

Titball et al.; Molecular Cloning and Nucleotide Sequence of the Alpha–Toxin (Phospholipase C) of Clostridium Perfringens, *Infection and Immunity*, 57(2):367–376 (1989).

Tizard et al.; Imaging of DNA Sequences with Chemiluminescence, *Proc. Natl. Acad. Sci.*, 87:4514–4518 (1990).

Tracy et al.; Dynamics of Rigid and Semirigid Rodlike Polymers, *Annu. Rev. Phys. Chem.*, 43:525–557 (1992).

Walker et al.; Stand Displacement Amplification–an Isothermal, in vitro DNA Amplification Technique, *Nucleic Acids Research*, 20(7):1691–1696 (1992).

Walker et al.; Isothermal in vitro Amplification of DNA by a Restriction Enzyme/DNA Polymerase System, *Proc. Natl. Acad. Sci.*, 89:392–396 (1992).

Wang et al.; Electrochemical Measurements of Oligonucleotides in the Presence of Chromosomal DNA Using Membrane–Covered Carbon Electrodes, *Anla. Chem.*, 69(19):4056–4059 (1997).

Waring; Complex Formation Between Ethidium Bromide and Nucleic Acids, *J. Mol. Biol.*, 13:269–282 (1965).

Hot Prospect for New Gene Amplifier, *Science*, 254:1292–1293 (1991).

Levicky et al.; Using Self–Assembly To Control the Structure of DNA Monolayers on Gold: A Neutron Reflectivity Study, *J. Am. Chem. Soc.*, p. est: 5.5.

Napier et al.; Modification of Electrodes with Dicarboxylate Self–Assembled Monolayers for Attachment and Detection of Nucleic Acids, *Langmuir*, 13(23):6342–6344 (1997).

Laibinis et al.; Orthogonal Self–Assembled Monolayers: Alkanethiols on Gold and Alkane Carboxylic Acids on Alumina, *Science*, 245:845–847 (1989).

Folkers et al.; Self–Assembled Monolayers of Long–Chain Hydroxamic Acids on the Native Oxides of Metals, *Langmuir*, 11(3):813–824 (1995).

Tarlov et al.; Electron–Transfer Reaction of Cytochrome c Adsorbed on Carboxylic Acid Terminated Alkanethiol Monolayer Electrodes, *J. Am. Chem. Soc.*, 113(5):1847–1849 (1991).

Yan et al.; Semiconductor–Based Interfacial Electron–Transfer Reactivity: Decoupling Kinetics from pH–Dependent Band Energetics in a Dye–Sensitized Titanium Dioxide/Aqueous Solution System, *J. Phys. Chem.*, 100(17):6867–6870 (1996).

Gao et al.; Self–Assembled Monolayers of Alkylphosphonic Acids on Metal Oxides, *Langmuir*, 12(26):6429–6435 (1996).

Lukes et al.; Direct Reaction of Phosphorus Acids with Hydroxy of a Silanol and on the Silica Gel Surface, *J. Am. Chem. Soc.*, 116(5):1737–1741 (1994).

Hong et al.; Electrochemical Measurement of Electron Transfer Rates through Zirconium 1,2–Ethanediylbis(phosphonate) Multilayer Films on Gold Electrodes, *Langmuir*, 7(10):2362–2369 (1991).

Yang et al.; Growth and Characterization of Metal(II) Alkanebisphosphonate Multilayer Thin Films on Gold Surfaces, *J. Am. Chem. Soc.*, 115(25)11855–11862 (1993).

Xu et al.; Immobilization of DNA on an Aluminum(III) Alkanebisphosphonate Thin Film with Electrogenerated Chemiluminescent Detection, *J. Am. Chem. Soc.*, 116(18):8386–8387 (1994).

Gardner et al.; Systems for Orthogonal Self–Assembly of Electroactive Monolayers on Au and ITO: An Approach to Molecular Electronics, *J. Am. Chem. Soc.*, 117(26):6927–6933 (1995).

Steel et al.; Electrochemical Quantitation of DNA Immobilized on Gold, Page est: 7.2. undated.

Terrettaz et al.; w–Hydroxythiol Monolayers at Au Electrodes. 5. Insulated Electrode Voltammetric Studies of Cyano/Bipyridyl Iron Complexes, *J. Phys. Chem.*, 99(28):11216–11224 (1995).

Herne et al.; Characterization of DNA Probes Immobilized on Gold Surfaces, *J. Am. Chem. Soc.*, 119(38):8916–8920 (1997).

\* cited by examiner

MONOLAYER AND ELECTRODE FOR DETECTING A LABEL-BEARING TARGET AND METHOD OF USE THEREOF

CROSS-REFERENCE TO RELATED APPLICATIONS

The instant application is a continuation-in-part of application Ser. No. 09/179,665, filed Oct. 27, 1998 now U.S. Pat. No. 6,132,971, which is a divisional application of Ser. No. 08/667,338, filed Jun. 20, 1996, now U.S. Pat. No. 5,871,918; which is a continuation-in-part of application Ser. No. 08/495,817, filed Jun. 27, 1995 (now abandoned); and a continuation-in-part of application Ser. No. 08/950,503, filed Oct. 14, 1997, now U.S. Pat. No. 5,968,745, which is a continuation-in-part of application Ser. No. 08/667,338, filed Jun. 20, 1996, now U.S. Pat. No. 5,871,918, the disclosures of which applications are incorporated herein by reference in their entirety.

BACKGROUND OF THE INVENTION

1. Field of the Invention

This invention relates to modified electrodes for analysis of binding pair interactions and the use of these electrodes, especially in nucleic acid analysis and protein-protein interactions.

2. Description of the Related Art

The present invention relates to electrodes for detecting interactions between members of a binding pair, which electrodes have been modified by formation of a non-conductive self-assembled monolayer, and to the method of detecting biomolecules, such as nucleic acids or other targets, including receptors, ligands, antigens or antibodies, utilizing such electrodes.

The detection of nucleic acid hybridization at solid surfaces has been used for the identification of infectious organisms in clinical specimens (Spargo, C. A. et al., 1993, *Molecular and Cellular Probes* 7, 395–404; Martin, W. J., 1994, Infectious Diseases, In *The Polymerase Chain Reaction* (K. B. Mullis, F. Ferre and R. A. Gibbs, eds.), pp. 406–417, Berkhauser, Boston), the quantitation of mRNA for gene expression analysis (Schena, M., et al., 1995,. *Science* 270, 467–470), and the sequencing or resequencing of genomic DNA on high-density "chip" arrays (Chee, M., et al., 1996, *Science* 274, 610–613). The disclosures of the publications and patent applications referred to herein are incorporated herein by reference. Presently, this detection involves the attachment of a fluorescent label to the target nucleic acid, which is then hybridized with a probe-modified surface and detected after washing the unhybridized DNA away from the solid surface. Since detection of photons is required for detection of hybridization, analysis of arrays labeled in this manner requires high-resolution fluorescence microscopes. Alternatively, indirect detection of hybridization can be accomplished using sandwich assays where the surface-bound hybrid is subsequently hybridized to an additional signal probe that carries one or more fluorescent labels or enzymes that convert a non-fluorescent substrate to a fluorescent one (Spargo, C. A. et al., 1993, *Molecular and Cellular Probes* 7, 395–404). By attaching multiple enzymes to the signal probes, large signal amplification can be achieved (Holodniy, M. et al., 1995, *J. Virology* 69, 3510–3516); however, the preparation of these multiple enzyme systems is complex.

Other workers have developed a gene detection method utilizing a nucleic acid probe immobilized on a carrier and a specific recognizing substance for double-stranded nucleic acid, but these methods do not allow recognition of single-stranded targets because intercalation of the reporter group in the nucleic acid is required (Hashimoto et al., U.S. Pat. No. 5,776,672).

The patents of Heller (U.S. Pat. Nos. 5,532,129; 5,565,322; 5,605,662; and 5,632,957) disclose the use of an electrode with a permeation layer which is an agarose gel placed on the electrode. Application of a potential to the electrode brings probe or target nucleic acid to the reaction site on the electrode but is not part of the detection step which proceeds via use of fluorescent probes.

Organosilanes may be covalently attached at selected positions of a hydroxylated surface of a substrate, such as silicon dioxide, to form an organosilane monolayer or bilayer film or coating, as set forth in the patent of Chrisey et al. (U.S. Pat. No. 5,688,642). Organosilanes are used that have at least one reactive site for binding to the hydroxylated surface of the substrate and another reactive site that is incapable of binding either to other organosilane molecules of the coating or to the substrate, but is available for binding to a molecule distinct from these, such as a nucleic acid modified by the addition of a thiol or amino group.

Labeled proteins and soluble reagents have been used to detect protein-protein interactions. For example, the patent of Weetall (U.S. Pat. No. 5,066,372) discloses a support layer on a working electrode that is porous to reagents and to which protein can be immobilized. See also U.S. Pat. No. 4,945,045 of Hill, U.S. Pat. No. 4,545,382 of Higgins, and U.S. Pat. No. 5,378,628 of Gratzel.

The paper of Wang et al. (Wang et al., 1997, *Anal. Chem.* 69, 4056–4059), describes a membrane-covered carbon electrode for analysis of oligonucleotides in the presence of polymeric nucleic acids. The purpose of the membrane is to exclude the polymeric DNA, while small molecules can pass through the membrane for electroanalysis by the carbon electrode. The membrane is not used for attachment of probes and the membrane-covered electrodes do not offer discrimination at the sequence level.

The parent applications, whose entire specifications, drawings, and claims are specifically incorporated herein by reference, disclose, among other inventions, sequencing and methods of qualitatively and quantitatively detecting nucleic acid hybridization. Such inventions represent a major advance in the art and provide oxidation-reduction complexes which function in a catalytic manner without the addition of an enzyme or fluorescent label, provide for a catalytic current to give the concentration of guanine, or alternate base, in a manner useful for determining the presence or absence of a target nucleic acid, and provide for extremely accurate testing.

The formation of self-assembled monolayers on surfaces has enabled the design of new interfaces for the study of specific redox-active analytes, solar energy conversion and fundamental electrochemistry. Prior monolayers have been formed via alkanethiol-gold linkage and related linkages between carboxylates and phosphonates and metal oxide surfaces, such as tin-doped indium oxide. Thus, self-assembly has been used to control the structure of oligomeric DNA monolayers on gold in high salt concentrations with DNA functionalized at the 5' end with a thiol group connected to the oligonucleotide by a hexamethylene linker. The DNA apparently remains attached through its thiol end group while contacts between DNA backbones and the surface are prevented by the formation of a mercaptohexanol monolayer. The oligomeric nucleic acid probe readily hybridizes to its complementary sequence. (Levicky, R. et al., 1998, *J. Amer. Chem. Soc.*, 120, 9787). Other systems that have been designed utilizing direct electron transfer from nucleic acids which have been contacted with an electrode, but do not use mediated electron transfer nor a self-assembled monolayer include those of Hall et al., PCT/GB93/00631.

For use in surface modification of wide-bandgap semiconductors or for interrogating interfacial electron-transfer reaction kinetics, carboxylate-functionalized ruthenium bipyridyl complexes may be used together with high-area nanocrystalline titanium dioxide films as one way to obtain surface attachment. Another way to accomplish surface attachment to nanocrystalline $TiO_2$ in film (electrode) or colloidal form, and for subsequent retention of the molecule over a wide pH range is hexaphosphonation of $Ru(bpy)_3^{2+}$ (Yan, S. G. et al., 1996, *J. Physical Chem.*, 100, 6867). This prior technique does not relate to mediated solution electrochemistry as in the current invention, but rather relates to direct electron transfer, using light as a stimulus instead of a voltage.

Prior work with self-assembled monolayers has included formation of monolayers terminated by constituents such as methyl or hydroxide to which members of binding pairs could not be bound and which are used for purposes different from, and generally inconsistent with, the binding of biomolecules to the monolayers. For example, self-assembled monolayers of long-chain alkanehydroxamic acids adsorbed on metal oxides, and terminated by methyl or hydroxyl, have been used for corrosion inhibition on the metals (Folkers, J. P. et al., 1995, *Langmuir*, 11, 813 and Laibinis, P. E. et al., 1989, *Science*, 245, 845) and self-assembled thiol-terminated monolayers have been formed that bind metals electrostatically (Tarlov, M. J. and Bowden, E. F., 1991, *J. Am. Chem. Soc.*, 113, 1847).

Early work related to the invention described herein was done with the formation of monolayers of 1,12-dodecanedicarboxylic acid (DDCA) on indium tin oxide (ITO) electrodes, with the electrodes being further derivatized with DNA via reaction of the pendant carboxylate with endogenous amines of the nucleobases following activation with water-soluble carbodiimide (Napier, M. et al., 1997, *Langmuir*, 13, 6342). The attachment of DNA to the electrode leads to a large catalytic enhancement due to the oxidation of guanine by the oxidized metal complex $Ru(bpy)_3^{3+}$. The carboxylate-ITO interface is compatible with the electrochemistry of $Ru(bpy)_3^{2+/3+}$ at $E_{1/2}=1.05$ V (vs Ag/AgCl), which would not be the case with gold-thiol monolayers. However, the 1,12 dodecane dicarboxylic acid monolayer is not stable under thermal stress, and, compared to the phosphonate of the invention herein, the carboxylate monolayer does not form reproducibly due to its lower stability.

Prior to the invention herein, self-assembled monolayers had not been described that allowed for straightforward attachment of oligonucleotide probes and the electrochemical detection of immobilized DNA via guanine oxidation. The self-assembled monolayers of this invention are thermally stable, oxidation resistant, and are formed rapidly and reproducibly. When carboxylate is used as the terminal group, nonspecific binding is minimized. Furthermore, the preferred phosphonate compounds which are used in the invention were previously unavailable or very difficult to synthesize (with only the $C_3$ carboxy phosphonate and the $C_3$ amino phosphonate being known to be commercially available).

Prior work with other phosphonate compounds has been in solution, for example, to enhance chromatographic separation (Lukes, I. et al., 1994, *J. Am. Chem. Soc.*, 116, 1737), to form insulating multilayer films (e.g., thiol phosphonate in Hong, H-G, et al., 1991, *Langmuir*, 7, 2362, and metal alkanebisphosphonate in Yang, H. C. et al., 1993, *J. Am. Chem. Soc.*, 115, 11855) or insulating monolayers (Kayyem, J. et al., PCT/US97/20014, to provide a passivation agent on the electrode surface that distances the oligonucleotide from the electrode, keeps charge carriers away from the surface of the electrode and blocks solvent accessibility to the electrode so that electron transfer only occurs at desired locations), or to study the reaction of phosphonic acid with a metal surface (Gao, W. et al., 1996, *Langmuir*, 12, 6429). Systems for orthogonal self-assembly of functionalized thiols, carboxylic acids or phosphonic acid, tagged, for example, with ferrocene were studied by Gardner, T. J. et al., 1995, *J. Am. Chem. Soc.*, 117, 6927. None of this work relates to binding of a member of a binding pair to a self-assembled phosphonate monolayer on an electrode. Where DNA has been immobilized on such a prior film, it has been via intercalation of the DNA in double-stranded DNA by electrostatic binding and not by covalent attachment (Xu, X-H et al., 1994, *J. Am. Chem. Soc.*, 116, 8386).

Other work with layers on electrodes relates not to monolayers but either to bilayers, for example, investigating lipid containing bilayers assembled on $SiO_2$ and the interactions of ligands with biomolecules (Boxer et al., PCT/US97/21835), or bilayers having a space between the membrane and the electrode used to detect selected nucleic acid sequences (Harding et al., PCT/AU97/00316); to polymerized layers (Ribi (EP 0 402 917 B1) using biosensors employing electrical, optical and mechanical signals having an electrically conductive surfactant layer to which are bound members of a specific binding pair, which may be present as a uniformly oriented layer that is electrically conducting as a result of polymerization of polyunsaturated groups in the surfactant film, formed by standard lipid monolayer technologies; or to semi-permeable membranes used for entirely different purposes (Maley et al., U.S. Pat. No. 5,711,868, in which an electrochemical sensor is used for sensing glucose by an enzyme in which the working electrode is covered with a semi-permeable membrane).

It is therefore an object of the invention to provide a method of immobilizing an oligonucleotide probe or protein-binding substance on the surface of an electrode, such as ITO, so that they are available for hybridization to a target nucleic acid or binding to a target protein, and subsequent detection via an oxidation-reduction reaction.

It is a further object of the invention to provide a method of making a non-conductive self-assembled monolayer on an electrode that may be used for the detection and quantitation of target biomolecules, such as nucleic acids or other targets, including receptors, ligands, antigens or antibodies.

Other objects and advantages will be more fully apparent from the following disclosure and appended claims.

SUMMARY OF THE INVENTION

The invention herein is a self-assembled phosphonate monolayer on an electrode, which in the preferred embodiment is a carboxy-alkyl phosphonate on an ITO surface, to which a member of a binding pair is covalently bound. The invention herein also includes a method of using the monolayer material to form a self-assembled monolayer on an electrode surface and a method of immobilizing binding pair members on the modified electrode surface. The electrode with the self-assembled monolayer in a preferred embodiment is useful for the electrochemical detection of a preselected base in a nucleic acid and for determining the presence of a target nucleic acid in a sample. When contacted with the target nucleic acid, an oligonucleotide probe coupled to the self-assembled monolayer reacts with the target nucleic acid to form a hybridized nucleic acid on the modified electrode surface. The hybridized nucleic acid is reacted with a transition metal complex capable of oxidizing a preselected base in the hybridized nucleic acid in an oxidation-reduction reaction, the oxidation-reduction reaction is detected; and the presence or absence of hybridized nucleic acid determined from the detected oxidation-reduction reaction. The oxidation-reduction reaction can be detected in accordance with the present invention because following the transfer of electrons from the immobilized binding pair to the transition metal complex, the monolayer permits the transition metal complex to transport the electrons to the surface of the electrode, where they are detected. Thus, the self-assembled monolayer is non-conductive, serves to immobilize reactants near the electrode surface, and allows the transition metal complex to move freely from the immobilized reactants to the conductive working surface of the electrode to permit electron transfer. In some instances, amplification techniques as are known in the art may be used in conjunction with the invention.

The invention may also be used to detect other targets (e.g, receptors, ligands, antigens, antibodies, etc.). For example, target protein in a sample may be detected by reacting the target protein with a protein binding substance such as an antibody attached to the self-assembled monolayer of the invention, followed by addition of a second protein-binding substance such as a second antibody that has bound to it a label capable of being oxidized in an oxidation-reduction reaction. As with nucleic acids, the label is reacted with a transition metal complex capable of oxidizing the label in an oxidation-reduction reaction. Detection of the oxidation-reduction reaction allows determination of the presence or absence of the target protein. One label suitable for use in this invention is an oligonucleotide.

Other objects and features of the inventions will be more fully apparent from the following disclosure and appended claims.

DETAILED DESCRIPTION OF THE INVENTION AND PREFERRED EMBODIMENTS THEREOF

Figure 1A:
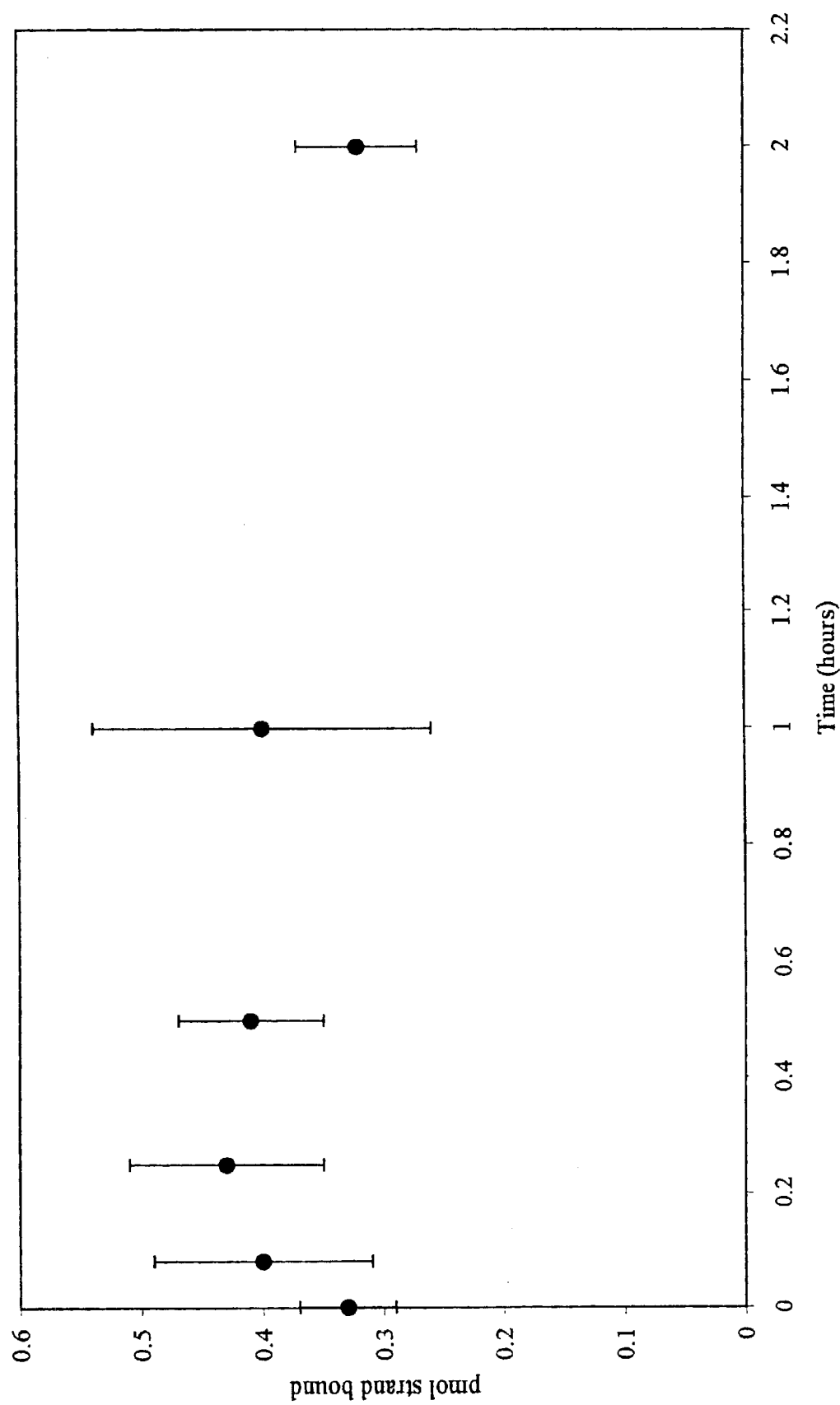
FIGS. 1a and 1b are graphs of the amount of guanine-containing oligonucleotide bound, in picomoles, versus assembly time of the self-assembled monolayer of the invention, illustrating the effect of self-assembly time on monolayer formation as a function of the amount of oligonucleotide probe that the monolayer is able to bind.

The present invention provides a self-assembled phosphonate monolayer with a covalently bound member of a binding pair on an electrode and the method of use of these self-assembled monolayers.

As used herein, the term non-conductive "monolayer" includes a single layer covering the conductive working surface of the electrode, preferably comprising alkyl phosphonate self-assembled from solution onto an ITO electrode surface, in what has been termed a "dative" or "coordination" bond between the oxygens on the phosphonate and metal atoms in the electrode (in the preferred embodiment). Formation of the monolayer of the invention does not include formation of truly covalent bonds, such as are found between two non-metals, such as C, N and O, which are able to share electrons to form a true covalent bond. The invention herein also does not include polymer membranes.

Specifically, the self-assembled monolayer of the invention is formed from phosphonate molecules capable of adhering to and modifying an electrode, such as an ITO electrode. The molecules used in the invention are multifunctional having at the minimum at least one surface-active functional group that bonds to the ITO surface, preferably phosphonate, and at least one end terminal group, $R_1$, such as carboxy, amino, hydroxyl or methyl, to which a member of a binding pair is covalently bound. In addition, these molecules may have an organic spacer $R_2$, preferably containing one or more carbon atoms and the associated substituents (generally hydrogen), between the phosphonate group and the $R_1$ group. Preferably the phosphonate monolayer comprises a carboxy-alkyl phosphonate (where $R_1$=—$CO_2H$ and $R_2$=—$(CH_2)_n$=), and, as discussed in more detail below, most preferably is 11-carboxyundecane phosphonic acid (where $R_1$=—$CO_2H$ and $R_2$=—$(CH_2)_{11}$—). As used herein, the term "member of a binding pair" includes all biomolecules which can bind to one another such as nucleic acids, receptors, ligands, antibodies, antigens and carbohydrates. While the examples herein primarily relate to use of oligonucleotides, one of ordinary skill in the art could use these examples and the disclosure herein for other biomolecules.

The electrode used in the invention comprises a conductive substrate or a substrate with the outer surface functioning as a conductive working surface. The substrate may itself be conductive or it may be nonconductive but have a conductive working surface. The electrode can have any shape that is conventional in this art, such as a cylindrical electrode having a conductive working surface on the exterior thereof or a flat sheet having the conductive working surface formed on one side thereof. The conductive substrate upon which the monolayer is assembled can be any metal or non-metal material conventionally used, including carbon, such as graphite, glassy carbon, pyrolytic graphite, carbon paste, and carbon fiber; doped and undoped oxides, such as indium-doped tin oxide (ITO), tin oxide, titanium oxide, manganese oxide, and lead oxide; and semiconductor materials, such as Si, Ge, ZnO, CdS, $TiO_2$, and GaAs; and the like. It is preferred to use ITO because its properties are relatively well-known, because it is inexpensive, and because it has a high oxidative potential limit in water at neutral pH and a relatively low charging current. The invention will be further described in connection therewith. Metals such as gold having adsorbed thiols or disulfides cannot be used with this invention, because they will oxidize at potentials lower than those needed for guanine oxidation.

An apparatus for determination of the presence of a label-bearing target may, for example, include a sample container for holding a fluid sample; an electrode, comprising a substrate having a conductive working surface thereon; and a non-conductive self-assembled monolayer on said conductive working surface, said monolayer comprising phosphonate molecules, each of which phosphonate molecules has at the minimum at least one phosphonate group and at least one $R_1$ group, where the $R_1$ group is covalently bound to a member of a binding pair, through which monolayer a transition metal complex can freely move from immobilized reactants to the conductive working surface to transfer electrons to the conductive working surface; and a potentiostat in electronic communication with the monolayer. The apparatus further comprises a member of a binding pair, such as an oligonucleotide probe attached to the self-assembled monolayer or a protein-binding substance attached to the self-assembled monolayer.

Generally, the method of determining the presence of a target nucleic acid in a sample comprises contacting a monolayer self-assembled on an electrode with an oligonucleotide probe so that the oligonucleotide probe becomes covalently attached to the monolayer; contacting the probe-modified monolayer on the electrode with the nucleic acid solution so that the target nucleic acid and the oligonucleotide probe form a hybridized nucleic acid on the modified electrode; reacting the hybridized nucleic acid with a transition metal complex capable of oxidizing a preselected base in the hybridized nucleic acid in an oxidation-reduction reaction; detecting the oxidation-reduction reaction; and determining the presence or absence of the nucleic acid from the detected oxidation-reduction reaction. Alternatively, the oligonucleotide probe may be coupled to the phosphonate before monolayer assembly on the electrode.

For proteins, determining the presence of a target protein in a sample comprises contacting a monolayer self-assembled on an electrode with a protein-binding substance so that the binding substance becomes covalently attached to the monolayer according to the invention; contacting the protein-modified monolayer on the electrode with the sample; contacting the modified electrode with a second protein-binding substance that has been modified to contain a label; reacting the monolayer with a transition metal complex capable of oxidizing the label in an oxidation-reduction reaction; detecting the oxidation-reduction reaction; and determining the presence or absence of the target protein from the detected oxidation-reduction reaction. One label suitable for use in this invention is an oligonucleotide. Alternatively, the protein-binding substance may be coupled to the phosphonate monolayer before monolayer assembly on the electrode.

Phosphonates

As discussed earlier, the molecules forming the self-assembled monolayer of the invention comprise a phosphonate group ($-PO_3H_2$), which bonds to the ITO electrode surface, and an $R_1$ group, which is capable of covalent bonding with a member of a binding pair. The phosphonate group may be monophosphonate, diphosphonate, triphosphonate, tetraphosphonate, or polyphosphonate moieties. The $R_1$ terminal group includes, but is not limited to, carboxyl, acid halide, acid anhydride, hydroxyl, epoxide, aldehyde, ketone, sulfhydryl, nitrile and amino groups. Preferably, the phosphonate group and $R_1$ are bridged by the organic spacer or linker $R_2$, which, when present, may comprise alkyl, alkenyl, alkynyl, and aromatic structures, that may be linear, branched, cyclic or polymeric structures. $R_2$ may be substituted with any number of phosphonate molecules that can bind to the ITO surface.

Preferably the phosphonate source is a carboxy-alkyl phosphonate. In the self-assembled monolayer of the invention, the phosphonate portion of a carboxy-alkyl phosphonate binds to ITO, with increased stability as the number of carbons in the alkyl portion increases. The carboxy moiety gives a negative charge to the monolayer and it is the carboxy group that couples to the member of the binding pair. An amino-alkyl phosphonate can be used if a positive monolayer charge is desired and a methyl or hydroxyl phosphonate can be used for a neutral surface charge.

The carboxy-alkyl phosphonate that is most preferred, based on tests done to date, is the 12-carbon carboxy-alkyl phosphonate (also referred to herein as 11-carboxyundecane phosphonic acid)(see Example 2 for preferred new method of preparation). This 12-carbon phosphonate was used primarily in the tests described in the Examples herein. Tests indicate that carboxy-alkyl phosphonates having 2–14 carbons in the alkyl group work to form a self-assembled monolayer with sufficient stability and the characteristics required for use in the invention herein. In order of decreased usefulness in the invention after the 12-carbon carboxy-alkyl phosphonate, judged when used alone in the monolayer are the 3-carbon amino-alkyl phosphonate and the 3-carbon carboxy-alkyl phosphonate. As the number of carbons in the chain of the phosphonate increases, there is increased stability of the resulting monolayer.

The synthesis of the carboxy-alkyl phosphonate as set forth in more detail in Example 2, generally involves: (1) converting bromoalkyl carboxylic acids to acid chloride intermediates by reaction with oxalyl chloride; followed by (2) converting the acid chloride intermediates into bromoalkyl esters by reaction with an alcohol, such as ethanol, under alkaline conditions so that (3) the bromoalkyl ester intermediates can be converted into carboxy-alkyl phosphonates by reaction with triethyl phosphite (or trimethyl phosphite) followed by acid hydrolysis to regenerate the acid.

The self-assembled phosphonate monolayer discussed in the examples herein is chemically homogeneous, i.e., consists of only carboxy-alkyl phosphonates. The invention includes, however, self-assembled heterogeneous monolayers in which these phosphonates are supplemented with other materials, for example, amino-alkyl phosphonates, hydroxy-alkyl phosphonates, methoxy-alkyl phosphonates, methyl-alkyl phosphonates, thiol-alkyl phosphonates, aldehyde-alkyl phosphonates, trifluoromethyl-alkyl phosphonates and zwitterionic phosphonates of various lengths, that alter the physical and chemical characteristics of the monolayer, for example, overall charge or charge distribution on the monolayer. These materials may or may not be capable of covalently bonding with a member of a binding pair. Mixed monolayers under specific conditions may enhance binding of specific target molecules to the member of the binding pair and/or reduce non-specific binding of non-target molecules to the electrode surface.

Test Samples

The method may be carried out on a test sample containing the target nucleic acid or other target biomolecules such as proteins. Any test sample suspected of containing the target may be used, including, but not limited to, tissue samples such as biopsy samples and biological fluids such as blood, sputum, urine and semen samples, bacterial cultures, soil samples, food samples, cell cultures, etc. The target may be of any origin, including animal, plant or microbiological (e.g., viral, prokaryotic, and eukaryotic organisms, including bacterial, protozoal, and fungal, etc.) depending on the particular purpose of the test. Examples include surgical specimens, specimens used for medical diagnostics, specimens used for genetic testing, environmental specimens, cell culture specimens, food specimens, dental specimens and veterinary specimens. The sample may be processed or purified prior to carrying out the instant method in accordance with techniques known or apparent to those skilled in the art; and nucleic acids therein may be digested, fragmented, and/or amplified (see below) prior to carrying out the instant method, if so desired.

Amplification

Inasmuch as the processes utilizing an electrode having a self-assembled monolayer according to the present invention involve contacting the target nucleic acid sample to an oligonucleotide probe to produce a hybridized nucleic acid, it may be desirable for certain applications using the invention to amplify the nucleic acid prior to contacting with the oligonucleotide probe. Amplification of a selected, or target, nucleic acid sequence may be carried out by any suitable means, such as those disclosed and discussed in the co-pending applications (Ser. Nos. 09/179,665 and 08/950,503).

Detection of Nucleic Acid

As noted above, an electrode of the invention herein on which the self-assembled monolayer has been formed, and methods of utilizing this electrode enable detection of hybridized nucleic acid. In this method, a target nucleic acid is contacted with an oligonucleotide probe bound to a self-assembled monolayer to form a hybridized nucleic acid. The oligonucleotide probes which are useful in the methods of the present invention can be any probe comprised of between about 4 or 6 bases up to about 80 or 100 bases or more, more preferably between about 8 and about 30 bases. Oligonucleotide probes may be prepared having any of a wide variety of base sequences according to techniques which are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 8-oxo-guanine, 6-mercaptoguanine, 4-acetylcytidine, 5-(carboxyhydroxyethyl)uridine, 2'-O-methylcytidine, 5-carboxymethylamino-methyl-2-thiouridine, 5-carboxymethylarninomethyluridine, dihydrouridine, 2'-O-methylpseudouridine, β,D-galactosylqueosine, 2'-O-methylguanosine, inosine, 7-deazaguanine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β,D-mannosylqueosine, 5-methoxycarbonylmethyluridine, 5-methoxyuridine, 2-methylthio-N6-isopentenyladenosine, N-((9-β-D-ribofuranosyl-2-methylthiopurine-6-yl)carbamoyl) threonine, N-((9-β-D-ribofuranosylpurine-6-yl)N-methylcarbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 5-methyluridine, N-((9-β-D-ribofuranosylpurine-6-yl)carbamoyl)threonine, 2'-O-methyl-5-methyluridine, 2'-O-methyluridine, wybutosine, 3-(3-amino-3-carboxypropyl)uridine, 2'-O-methyladenine, and 2'-O-methylinosine. Any oligonucleotide backbone may be employed, including DNA, RNA, modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates (for example, every other one of the internucleotide bridging phosphate residues may be modified as described). The oligonucleotide may be a "peptide nucleic acid" such as described in P. Nielsen et al., 1991, *Science* 254, 1497–1500. The only requirement is that the oligonucleotide probe should possess a sequence at least a portion of which is complementary to a portion of the sequence of the target nucleic acid. It may be desirable in some applications to contact the nucleic acid sample with a number of oligonucleotide probes having different base sequences (e.g., where there are two or more target nucleic acids in the sample, or where a single target nucleic acid is hybridized to two or more oligonucleotide probes in a "sandwich" assay).

Preselected Base

After hybridization, the target nucleic acid hybridized to the oligonucleotide probe attached to the monolayer self-assembled on the electrode is reacted with a suitable mediator which is capable of oxidizing a preselected base in an oxidation-reduction reaction. The preselected base can be any naturally occurring or synthetic nucleotide base which undergoes oxidation upon reaction with the selected mediator. The preselected base exhibits a unique oxidation rate when paired as compared to when the preselected base is unpaired. The preselected base should exhibit unique oxidation rates when paired with each of the four naturally occurring bases. Generally, bases whose 5'-mononucleotides (e.g., the 5'-deoxyribonucleotide or 5'-ribonucleotide) exhibit rate constants above $10^4 M^{-1} s^{-1}$ can be detected using the catalytic reaction. Examples of suitable preselected bases include but are not limited to guanine, adenine, 8-oxo-guanine, 8-oxo-adenine, 8-bromo-guanine, xanthine, pseudouridine, 6-mercaptoguanine, 8-mercaptoguanine, 2-thioxanthine, 6-thioxanthine, 6-mercaptopurine, 2-amino-6-carboxymethyl-mercaptopurine, 2-mercaptopurine, 6-methoxypurine, 2-acetylamino-6-hydroxypurine, 6-methylthio-2-hydroxypurine, 2-dimethylamino-6-hydroxypurine, 2-hydroxypurine, 2-aminopurine, 6-amino-2-dimethylallyl-purine, 2-thioadenine, 8-hydroxyadenine, and 8-methoxyadenine. Typically, the preselected base is selected from the group consisting of guanine, adenine, 6-mercaptoguanine, 8-oxo-guanine, and 8-oxo-adenine, with guanine being the currently preferred naturally occurring preselected base and 8-oxo-guanine or 6-mercaptoguanine the currently preferred synthetic preselected base.

Mediator

The mediator that is needed to enable electron transfer may be any molecule such as a cationic, anionic, non-ionic, or zwitterionic molecule which is reactive with the preselected base at a unique oxidation potential to transfer electrons from the nucleic acid to the electrode. Thus the selection of mediator will be dependent upon the particular preselected base chosen, and will be readily determinable by those skilled in the art. Particularly preferred mediators include transition metal complexes which are capable of metal-nucleic acid electron transfer with the preselected base such that the reduced form of the metal complex is regenerated, completing a catalytic cycle. Examples of suitable transition metal complexes for use in the methods of the present invention include, for example, Ruthenium$^{2+}$(2,2'-bipyridine)$_3$("Ru(bpy)$_3^{2+}$"), Ruthenium$^{2+}$(4,4'-dimethyl-2,2'-bipyridine)$_3$("Ru(Me$_2$-bpy)$_3^{2+}$"), Ruthenium$^{2+}$(5,6-dimethyl-1,10-phenanthroline)$_3$("Ru(Me$_2$-phen)$_3^{2+}$"), Iron$^{2+}$(2,2'-bipyridine)$_3$("Fe(bpy)$_3^{2+}$"), Iron$^{2+}$(5-chlorophenanthroline)$_3$ ("Fe(5-Cl-phen)$_3^{2+}$"), Osmium$^{2+}$(2,2'-bipyridine)$_3$("Os(bpy)$_3^{2+}$"), Osmium$^{2+}$(5-chlorophenanthroline)$_3$("Os(5-Cl-phen)$_3^{2+}$"), dioxorhenium$^{1+}$phosphine, and dioxorhenium$^{1+}$pyridine ("ReO$_2$(py)$_4^{1+}$"). Some anionic complexes useful as mediators are Ru(bpy)((SO$_3$)$_2$-bpy)$_2^{2-}$ and Ru(bpy)((CO$_2$)$_2$-bpy)$_2^{2-}$ and some zwitterionic complexes useful as mediators are Ru(bpy)$_2$((SO$_3$)$_2$-bpy) and Ru(bpy)$_2$((CO$_2$)$_2$-bpy) where (SO$_3$)$_2$-bpy$^{2-}$ is 4,4'-disulfonato-2,2'-bipyridine and (CO$_2$)$_2$-bpy$^{2-}$ is 4,4'-dicarboxy-2,2'-bipyridine. Suitable substituted derivatives of the pyridine, bipyridine and phenanthroline groups may also be employed in complexes with any of the foregoing metals. Suitable substituted derivatives include but are not limited to 4-aminopyridine, 4-dimethylpyridine, 4-acetylpyridine, 4-nitropyridine, 4,4'-diamino-2,2'-bipyridine, 5,5'-diamino-2,2'-bipyridine, 6,6'-diamino-2,2'-bipyridine, 4,4'-diethylenediamine-2,2'-bipyridine, 5,5'-diethylenediamine-2,2'-bipyridine, 6,6'-diethylenediamine-2,2'-bipyridine, 4,4'-dihydroxyl-2,2'-bipyridine, 5,5'-dihydroxyl-2,2'-bipyridine, 6,6'-dihydroxyl-2,2'-bipyridine, 4,4',4"-triamino-2,2',2"-terpyridine, 4,4',4"-triethylenediamine-2,2',2"-terpyridine, 4,4',4"-trihydroxy-2,2',2"-terpyridine, 4,4',4"-trinitro-2,2',2"-terpyridine, 4,4',4"-triphenyl-2,2',2"-terpyridine, 4,7-diamino-1,10-phenanthroline, 3,8-diamino-1,10-phenanthroline, 4,7-diethylenediamine-1,10-phenanthroline, 3,8-diethylenediamine-1,10-phenanthroline, 4,7-dihydroxyl-1,10-phenanthroline, 3,8-dihydroxyl-1,10-phenanthroline, 4,7-dinitro-1,10-phenanthroline, 3,8-dinitro-1,10-phenanthroline, 4,7-diphenyl-1,10-phenanthroline, 3,8-diphenyl-1,10-phenanthroline, 4,7-disperamine-1,10-phenanthroline, 3,8-disperamine-1,10-phenanthroline, dipyrido[3,2-a:2',2'-c]phenazine, 6,6'-dichloro-2,2'-bipyridine, phthalocyanines and porphyrins.

Oxidation-reduction Reaction

The mediator may be reacted with the hybridized nucleic acid under conditions sufficient to effect the oxidation-reduction reaction of the mediator with the preselected base. The solvent in which the oxidation-reduction reaction takes place may be any suitable solvent for solubilizing nucleic acids, and preferably comprises water. Suitable conditions for permitting the oxidation-reduction reaction to occur will be known to those skilled in the art.

Detection of Oxidation-reduction Reaction

The occurrence of the oxidation-reduction reaction may be detected on an electrode having a self-assembled monolayer in accord with the present invention to observe a change in the electronic signal which is indicative of the occurrence of the oxidation-reduction reaction. The electrode is placed in contact with the solution of mediator and generally, a reference electrode and an auxiliary electrode are also placed in contact with the solution in conjunction with the working electrode (with most of the current passing through the auxiliary electrode). Similarly, suitable reference electrodes will also be known in the art and include, for example, silver/silver chloride electrodes. A suitable auxiliary electrode is a Pt electrode.

The detection of the electronic signal associated with the oxidation-reduction reaction permits the determination of the presence or absence of target. The step of determining the presence or absence of target typically includes (i) measuring the reaction rate of the oxidation-reduction reaction, (ii) comparing the measured reaction rate to the oxidation-reduction reaction rate of the transition metal complex with or without nucleic acid, and then (iii) determining whether or not the measured reaction rate is essentially the same as the oxidation-reduction reaction rate of the transition metal complex with or without target. The step of measuring the reaction rate may be carried out by any suitable means. For example, the relative reaction rate may be determined by comparing the current at the same scan rate, probe concentration, target concentration, mediator, buffer, temperature, and/or electrochemical method.

The oxidation-reduction reaction rate may be measured according to suitable means known to those skilled in the art. Typically, the oxidation-reduction reaction rate is measured by measuring the electronic signal associated with the occurrence of the oxidation-reduction reaction. For example, the electronic signal associated with the oxidation-reduction reaction may be measured by providing a suitable apparatus in electronic communication with an electrode coated with a self-assembled monolayer as disclosed herein. A suitable apparatus is a potentiostat capable of measuring the electronic signal which is generated so as to provide a measurement of the oxidation-reduction reaction rate of the reaction between the hybridized nucleic acid and the mediator. When a protein is the target to be detected, the detector has bound to it a label capable of being oxidized in an oxidation-reduction reaction, with one such label being an oligonucleotide containing the preselected base.

The electronic output may be characteristic of any electrochemical method, including cyclic voltammetry, normal pulse voltammetry, chronoamperometry, chronocoulometry, or square-wave voltammetry, with cyclic voltammetry and chronoamperometry being the currently preferred forms. A computer as is known in the art may be used for controlling the use of the electrode and for recording results of such use. The method most frequently used to analyze nucleic acids on monolayers self-assembled on ITO electrodes according to the invention is cyclic voltammetry. In cyclic voltammetry, the potential of the electrochemical system is varied linearly from an initial potential (0–800 mV) to a final potential (1300–2000 mV). When the final potential is reached, the scan direction is reversed and the same potential range is swept in the opposite direction. The potential is varied at a constant scan rate (for example, about 10 mV/s to about 5000 V/s). For the majority of experiments, the initial potential is set at 0 mV and the final potential experimentally determined by the scan rate. The currently preferred scan rate is 20 V/s with a 1600 mV final potential. The current is collected at each potential and the data is plotted as a current versus potential spectra.

As an alternative to cyclic voltammetry, potential step methods such as chronocoulometry or chronoamperometry may be used to analyze nucleic acids on monolayers of the invention. In chronocoulometry, the electrochemical system is stepped directly from the initial potential (0 mV–800 mV) to the final potential (1000 mV–1600 mV). The electrochemical system is held at the final potential for some specified period of time (50 $\mu$s to 30 s) and the charge is collected as a function of time. Although not currently done, if desired, the potential can be stepped back to the initial potential and the charge can be collected at the initial potential as a function of time. In chronoamperometry, the electrochemical system is stepped from an initial potential (0 mV–800 mV) directly to a final potential (1000–1600 mV) for some specified period of time (50 μs to 30 s) and the current is collected as a function of time. If desired, the potential can be stepped back to the initial potential, and the current can be collected at the initial potential as a function of time. The preferred potential step is 1100 mV with collection time of 500 ms although preferred potential steps and times may vary with different assay parameters.

Method of Detection

Detection of a preselected base on a target nucleic acid using an electrode with a non-conductive self-assembled monolayer according to the invention herein comprises (a) contacting the test sample to an oligonucleotide probe, bound to a monolayer according to the invention, that specifically binds to the target nucleic acid to form a hybridized nucleic acid; (b) contacting the hybridized nucleic acid to a transition metal complex that oxidizes the preselected base in an oxidation-reduction reaction; (c) detecting the presence or absence of the oxidation-reduction reaction associated with the hybridized nucleic acid; and (d) determining the presence or absence of the target nucleic acid in the test sample from the detected oxidation-reduction reaction at the preselected base.

Preferably, the target nucleic acid contains at least about 10 more of the preselected base than does the oligonucleotide probe, or more preferably at least 50 or 100 more of the preselected base than does the oligonucleotide probe. A larger current enhancement is advantageously obtained when the target nucleic acid contains many more of the preselected base than does the oligonucleotide probe.

The target nucleic acid is preferably longer than the oligonucleotide probe, and at least one of the preselected bases is "overhanging" as described in U.S. Pat. No. 5,871,918 and not hybridized to the oligonucleotide probe in the hybridized nucleic acid. Preferably, at least 10, 50, or 100 of the preselected bases are "overhanging" bases, thereby providing substantial amplification of the electrochemical signal detected.

Optionally, but preferably, the oligonucleotide probe sequence is free of the preselected base. Where such a sequence of naturally occurring bases that will conveniently hybridize to the target nucleic acid but does not contain the preselected base is not available, the strategy of employing alternate bases that are redox inactive (discussed below) may be employed.

For example, an oligonucleotide probe sequence that does not contain any guanine residues (e.g., only A, T, and C) may be chosen. The cyclic voltanunogram of $Ru(bpy)_3^{2+}$ in the presence of this strand is very similar to that without the oligomer. This oligonucleotide probe is then hybridized to a target nucleic acid strand that contains guanines in either the overlapping base-paired regions and/or in overhanging regions if the target nucleic acid is longer than the oligonucleotide probe. Because multiple guanines are detected, the signal is amplified relative to the number of hybrids formed. In a case where a genomic DNA or RNA is the target nucleic acid strand, large numbers of overhanging guanines are encountered, which would give tremendous signal amplification.

In a preferred embodiment, the assay for the preselected base on the target nucleic acid strand involves immobilization of the (preferably redox-silent) oligonucleotide probe strand on the self-assembled monolayer on the electrode surface, which provides a low background signal when scanned in the presence of the mediator. The monolayer is then contacted with a solution of the target nucleic acid, which contains the preselected base. If hybridization occurs, the target nucleic acid will now be in close proximity to the electrode, and a current enhancement will be detected in the presence of mediator.

An alternate base may be used that would substitute for guanine (i.e., a base that, like guanine, has a greater binding affinity for cytosine than do other bases in a nucleic acid duplex) in the oligonucleotide probe strand but would not be oxidized by the mediator under the applicable reaction conditions. When the preselected base in the target nucleic acid is guanine and the target nucleic acid also contains cytosine (which ordinarily bonds with guanine in the oligonucleotide probe), then the probe contains an alternate base that bonds to cytosine in the hybridized nucleic acid. The alternate base may be inosine which is three orders of magnitude less electrochemically reactive than guanine. The reacting step typically comprises reacting the transition metal complex with the nucleic acid under conditions sufficient to effect the selective oxidation of the preselected base without oxidizing the alternate base.

Thus, a method of detecting a target nucleic acid, where the target nucleic acid contains at least one preselected base, and the oligonucleotide probe contains alternate redox inactive bases, comprises: (a) contacting the target nucleic acid to a complementary oligonucleotide probe that specifically binds to the target nucleic acid to form a hybridized nucleic acid; (b) reacting the hybridized nucleic acid with a transition metal complex capable of oxidizing the preselected base in an oxidation-reduction reaction; (c) detecting the oxidation-reduction reaction; and (d) determining the presence or absence of the hybridized nucleic acid from the detected oxidation-reduction reaction at the preselected base.

Quantitating Nucleic Acids

The above-described method is particularly well suited to the quantitative detection of nucleic acids. In the case described in this section, the rate constant for oxidation of the hybridized nucleic acid by the mediator (e.g., $Ru(bpy)_3^{2+}$) can be determined from the cyclic voltammogram by digital simulation. Under most conditions, this reaction will obey second-order kinetics, so the rate=$k[Ru(bpy)_3^{2+}][DNA]$ where k is the rate constant that is specific for the particular oligonucleotide probe-target nucleic acid hybrid, $[Ru(bpy)_3^{2+}]$ is the concentration of the mediator, and [DNA] is the concentration of the hybridized nucleic acid (which could be a DNA-RNA hybrid). If k and $[Ru(bpy)_3^{2+}]$ are known, then the quantity of the hybridized nucleic acid can be determined. In practice, a calibration curve for current enhancements obtained with different quantities of standard solutions containing target nucleic acid is constructed and the current enhancement used to obtain the quantity of hybridized nucleic acid directly. This quantity is then related directly to the quantity of material containing target nucleic acid (e.g., infectious organism in a clinical sample). See, e.g., M. Holodniy et al., 1995, *J. Virol.* 69, 3510–3516; J. Mellors et al., 1996, *Science* 272, 1167–1170.

Use With Proteins

The monolayer self-assembled onto the conductive working surface of an electrode can also be used for detection of biomolecules other than nucleic acids such as proteins using the disclosure of the invention herein along with methods of working with proteins known to those of skill in the art. As with nucleic acids, no enzyme label is required for use of the invention with other biomolecules. For example, a method of detecting a target protein in a sample comprises: (a) attaching a protein-binding substance to a monolayer that has been self-assembled onto a conductive working surface;

(b) contacting the target protein to the protein-binding substance coupled to the monolayer; (c) contacting the target protein bound to the monolayer to a second protein-binding substance which has bound to it a label capable of being oxidized in an oxidation reduction reaction; (d) reacting the label on the second protein-binding substance bound to the target protein with a transition metal complex capable of oxidizing the label in an oxidation-reduction reaction; (e) detecting the oxidation-reduction reaction; and (f) determining the presence or absence of the target protein from the detected oxidation-reduction reaction.

The features of the present invention will be more clearly understood by reference to the following examples, which are not to be construed as limiting the invention.

EXAMPLES

Example 1
Reagents and DNA

Inorganic reagents used in these experiments were of analytical grade or higher. The sources of the reagents are as follows: carboxy-alkyl phosphonates made according to Example 2 or by Sigma Chemicals (St. Louis, Mo.) or Aldrich (Milwaukee, Wis.); 1-ethyl-3-(3-dimethylaminopropyl) carbodiimide (EDC), N-hydroxysuccinimide (NHS) and ethanolamine (Sigma or Aldrich); [$\gamma$-$^{32}$P] adenosine triphosphate (ATP)(Pharmacia Biotech, Inc., Piscataway, N.J.); water (Milli-Q Plus purification system of Millipore, Bedford, Mass.); synthetic oligonucleotides (Oligos Etc., Inc., Wilsonville, Oreg.); 1-bromododecanoic acid, N,N'-dimethylformamide, and triethyl phosphite (Sigma); oxalyl chloride, dichloromethane, anhydrous ethanol, and triethylamine (Aldrich); and $Na_2HPO_4$, $NaH_2PO_4$, NaCl and concentrated HCl (Fisher, Pittsburgh, Pa.).

Example 2
Preferred Method of C-12 Phosphonate Preparation

Although certain phosphonic acids are currently commercially available, for example, amino propyl phosphonic acid and 2-carboxy ethyl phosphonic acid (Sigma or Aldrich), it is preferred to utilize a higher carbon phosphonic acid, such as a 11-carboxyundecane phosphonic acid (C-12 phosphonate).

C-12 phosphonate can be prepared as follows: bromododecanoic acid, 1.12 g (4 mmoles) is dissolved in 10 mL dichloromethane in a 50-mL round-bottom flask. Oxalyl chloride (2 mL of 2M) is added with stirring under a nitrogen atmosphere at room temperature and the reaction is initiated by the addition of 100 µl N,N'-dimethylformamide (DMF). At one and two minutes after starting the reaction, an additional 100 µL of DMF is added to the solution. After 15 minutes, 8 mL dichloromethane is added to the reaction mixture and stirring continued under nitrogen for 15 minutes. The solvent is then removed from the acid chloride intermediate with a stream of nitrogen.

The acid chloride intermediate is immediately dissolved in 10 mL dichloromethane and while rapidly stirring, ethanol (350 µL) and triethylamine (835 µL) are added. The pH of the solution when tested with pH paper is between 7 and 8. The solution is stirred for one hour at room temperature. The solvent is evaporated off, and the product dissolved in 10 mL hexane and washed with 10 mL water. The hexane phase is recovered and evaporated to dryness to recover the ethyl ester intermediate.

Triethyl phosphite (1.5 mL) is added to the ethyl ester intermediate in a 100 mL round bottom flask and the solution is refluxed under nitrogen. After 1.5 hours, additional triethyl phosphite (1.5 mL) is added to the reaction mixture and refluxing under nitrogen is continued for 4.5 hours. The reaction mixture is cooled to approximately 50° C. and 13.2 mL concentrated HCl is added. After refluxing for 16 hours, the reaction mixture is pipetted into a beaker and 5 mL water is added. As the reaction mixture cools to room temperature, the 12-phosphonododecanoic acid product precipitates out of solution. The product is collected by filtration, washed with water and dried.

Example 3
Preparation of Monolayer on Electrodes

ITO electrodes on glass (Delta Technologies, Stillwater, Minn.) of desired size and shape, for example, 15 mm×15 mm squares with a resistivity of 10 ohms/square and an ITO layer 1400–1600 Angstroms thick with a 2000 Angstrom underlayer of $SiO_2$, are cleaned before use and allowed to air dry.

The cleaned and dried electrodes are exposed to a selected carboxy-alkyl phosphonate dissolved in an organic solvent (for example, methanol or ethanol) at room temperature. Methanol is preferred because carboxy-alkyl phosphonates are very soluble and self-assemble well from methanol. The concentration of carboxy-alkyl phosphonates ranges from 0.1 mM–20 mM with 2–5 mM carboxy-alkyl phosphonate preferred to provide sufficient monolayer formation. Suitable self-assembly times can vary from three seconds to 20 hours, with 30 minutes currently preferred. The unattached carboxy-alkyl phosphonate is rinsed off the ITO electrodes with three washes of water and the electrodes allowed to dry. If there is insufficient phosphonate, the monolayer may be poorly ordered and the carboxylate group may not be accessible for activation and oligonucleotide probe attachment. An excess of monolayer acts as a barrier to electron transfer by inhibiting the movement of the transition metal complex from the oligonucleotide to the electrode surface. Also, an excess of carboxy-alkyl phosphonate monolayer can lead to electrostatic inhibition of oligonucleotide probe binding and target hybridization.

The placement of reagents on to the monolayer/ITO electrode of the invention is standardized as known in the art, for example, by marking the electrode on the non-conductive side.

Example 4
Activation of Monolayer on Electrode

The ITO electrode having thereon the monolayer according to Example 3 is exposed to the activating/coupling compounds 1-ethyl-3-(3-dimethylaminopropyl) carbodiimide (EDC) and N-hydroxysuccinimide (NHS) in a molar ratio of 4:1. The concentration of EDC ranges from 20–400 mM and the concentration of NHS ranges from 5–100 mM. The currently preferred concentrations are 400 mM EDC and 100 mM NHS. Thirty microliters of the EDC/NHS solution is pipetted onto each ITO electrode/monolayer and incubated for 30 minutes at room temperature. The unattached EDC/NHS is rinsed off the ITO electrodes with three washes of water and then the electrodes are allowed to air dry.

Example 5
Attachment of DNA Probe

An oligonucleotide probe with an alkyl amine linker on the 3'- or 5'-end is coupled to the activated monolayer. The length of the alkyl amine should be at least three carbons, and preferably between three and twelve carbons with the currently preferred length being six carbons. The oligonucleotide probe (20 µL) at concentrations of 20 to 100 µM in 1M NaCl/0.25 M $NaHCO_3$, pH 9 is pipetted onto the activated monolayer and incubated at room temperature (approximately 25° C.) for 30 minutes. The oligonucleotide probe solution is removed and the electrode washed by immersion in water followed by washes in 0.1 M sodium phosphate buffer, pH 7, 1.0 M NaCl and water. The degree of oligonucleotide probe attachment to the monolayer can be assessed radiochemically by the addition of $^{32}$P-labelled oligonucleotide probe to the reaction mixture.

Activated carboxyl groups that did not react with oligonucleotide probe are blocked with ethanolamine to reduce non-specific target binding. The electrodes are immersed in 0.1 M ethanolamine, pH 8 at 25° C. for about 20 minutes. Ethanolamine is rinsed off the electrodes with three washes of water and the electrodes are allowed to air dry.

The concentration of oligonucleotide probe, the pH, incubation time, temperature and blocking agent can vary as would be clear to one of ordinary skill in the art.

Example 6
Exposure of Electrode to Target Nucleic Acid

A nucleic acid target, with a nucleic acid sequence that is complementary to a portion of the oligonucleotide probe sequence is allowed to hybridize to the probe. At present a complementary synthetic oligonucleotide that contains 23 guanines is being used. The target nucleic acid (20 μl in 0.8 M NaCl and 0.05 M NaH$_2$PO$_4$, pH 7.0) is pipetted onto the oligonucleotide probe/monolayer and incubated at 25° C. for an hour. The target nucleic acid solution is removed and the electrode washed in water followed by washes in 0.1 M NaH$_2$PO$_4$, pH 7.0, 1.0 M NaCl and water. The hybridization conditions may be varied as would be clear to one of ordinary skill in the art. The degree of target nucleic acid hybridization to the oligonucleotide probe can be assessed radiochemically by the addition of $^{32}$P-labelled target nucleic acid to the reaction mixture.

Example 7
Electrochemistry of Electrodes

The currently preferred method of electrochemically interrogating the electrodes is cyclic voltammetry, although electrochemical interrogation methods such as chronoamperometry, chronocoulometry and step voltammetry are also useful. Cyclic voltammetry is performed on each ITO electrode as follows. Suitable scan speeds include scan speeds of about 50 mV/s–5000 V/s, with a preferred scan rate of 20 V/s. At this scan rate, there is a maximum signal from bound DNA and a minimum signal from the background. The potential is first swept in the positive direction, with a starting potential of 0 V and switching potential between 1.3 and 1.8 V depending on the scan speed. A three-electrode setup is used: a Ag/AgCl reference electrode, a Pt wire auxiliary electrode, and a modified ITO working electrode according to the invention. The modified ITO electrode is placed in an electrochemical cell, and 200 μL of 100 μM Ru(bpy)$_3^{2+}$ in 50 mM sodium phosphate buffer (pH 7.0) is placed above the modified electrode. The buffer may contain NaCl (generally up to about 1 M or as desired for the particular system under study) which in some cases increases signal separation. The reference electrode and Pt electrode are placed in the electrochemical cell in contact with the Ru(bpy)$_3^{2+}$ solution. The sample is interrogated, and the data collected, stored and analyzed.

Example 8
Monolayer Formation Evaluation

Figure 1B:
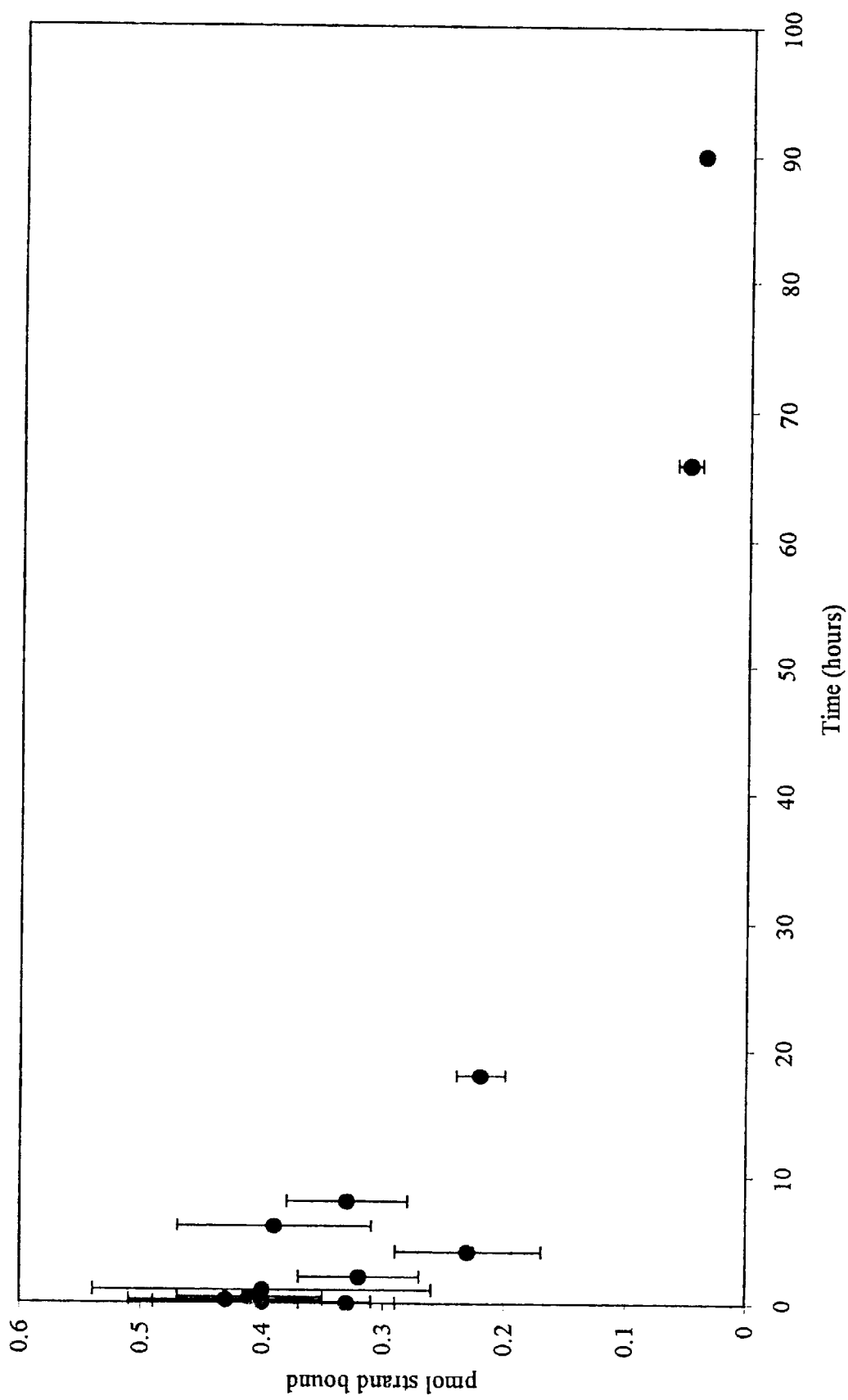

FIGS. 1a and 1b show the effect of self-assembly time on monolayer formation as indicated by the amount of oligonucleotide probe that the monolayer is able to bind, in picomoles. FIG. 1a is for self-assembly times up to 2 hours and FIG. 1b is for times up to 90 hours. The amount of oligonucleotide probe bound to the monolayer is an indirect measure of monolayer formation. For self-assembly times up to approximately 10 hours, the self-assembly time does not appear to impact substantially on the ability of the monolayer to bind oligonucleotide probe. After 20 hours of self-assembly, the ability of the monolayer to bind oligonucleotide probe drops off dramatically. The amount of oligonucleotide probe bound to the monolayer was found to be constant for incubation times from 3 seconds to 10 hours.

Figure 2:
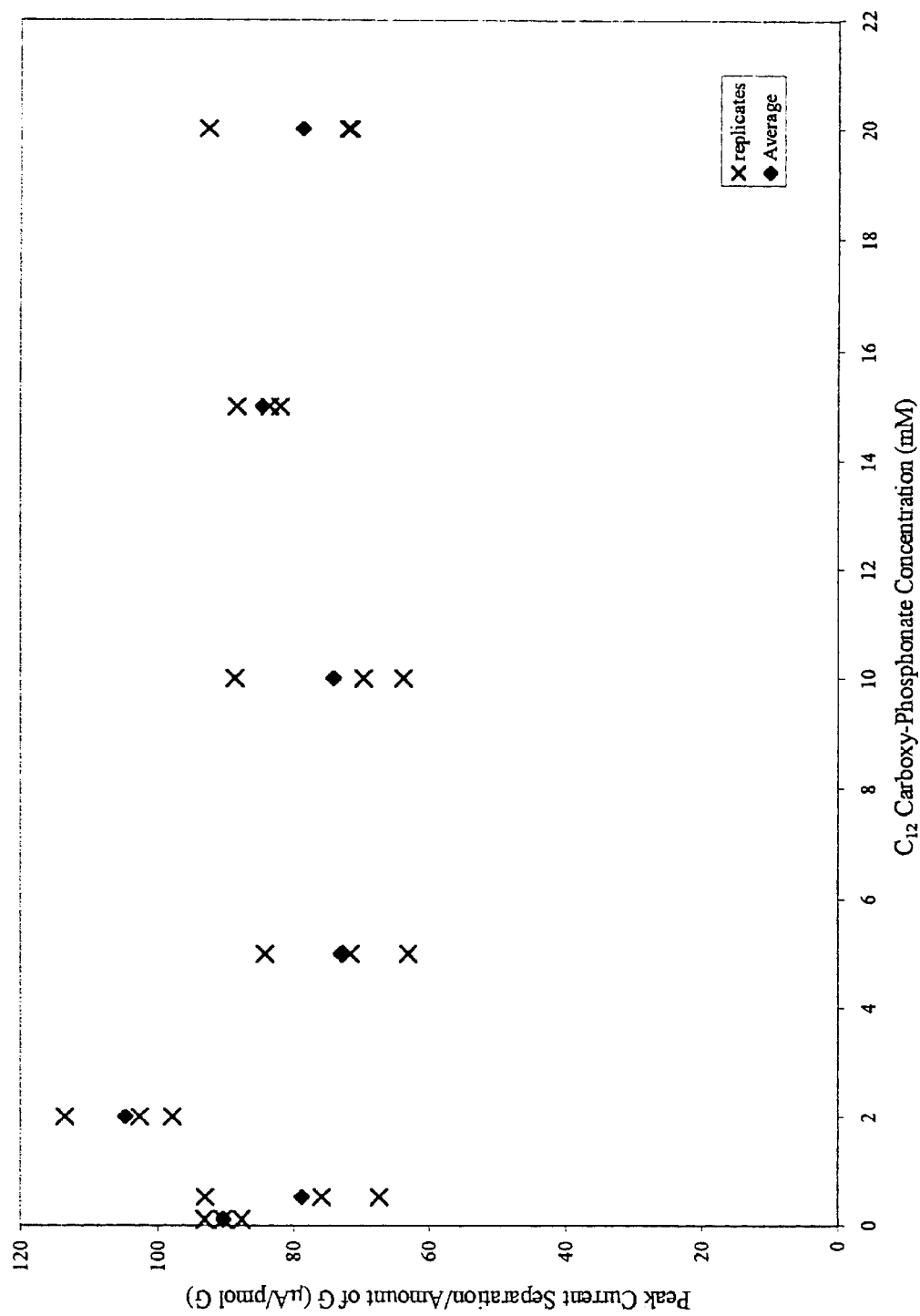
FIG. 2 graphically illustrates the effect of the concentration of $C_{12}$ carboxyphosphonate in the self-assembly solution on monolayer formation, as indicated by the electrochemical response of the guanine-containing oligonucleotide coupled to the self-assembled monolayer. Electrochemical measurements were made using cyclic voltammetry at a scan speed of 20 V/s and a $Ru(bpy)_3^{2+}$ concentration of 100 $\mu$M.

Monolayer formation was evaluated as a function of the concentration of phosphonate solution to which the electrode is exposed. This evaluation was conducted by examining current above background (current separation) per pmole of guanine of the oligonucleotide strand as shown in FIG. 2. The monolayers were formed using a 2-hour self-assembly time at all concentrations and electrochemical measurements were made using cyclic voltammetry at 20 V/s and a Ru(bpy)$_3^{2+}$ concentration of 100 μM. The electrochemical response was measured as μA of peak separation over background per picomole of guanine coupled to the monolayer. Concentrations of the 12-carbon carboxyalkyl phosphonate in the self-assembly solution ranged from 0.1 to 20 mM. The effect of the concentration of the phosphonate solution was minimal.

Figure 3:
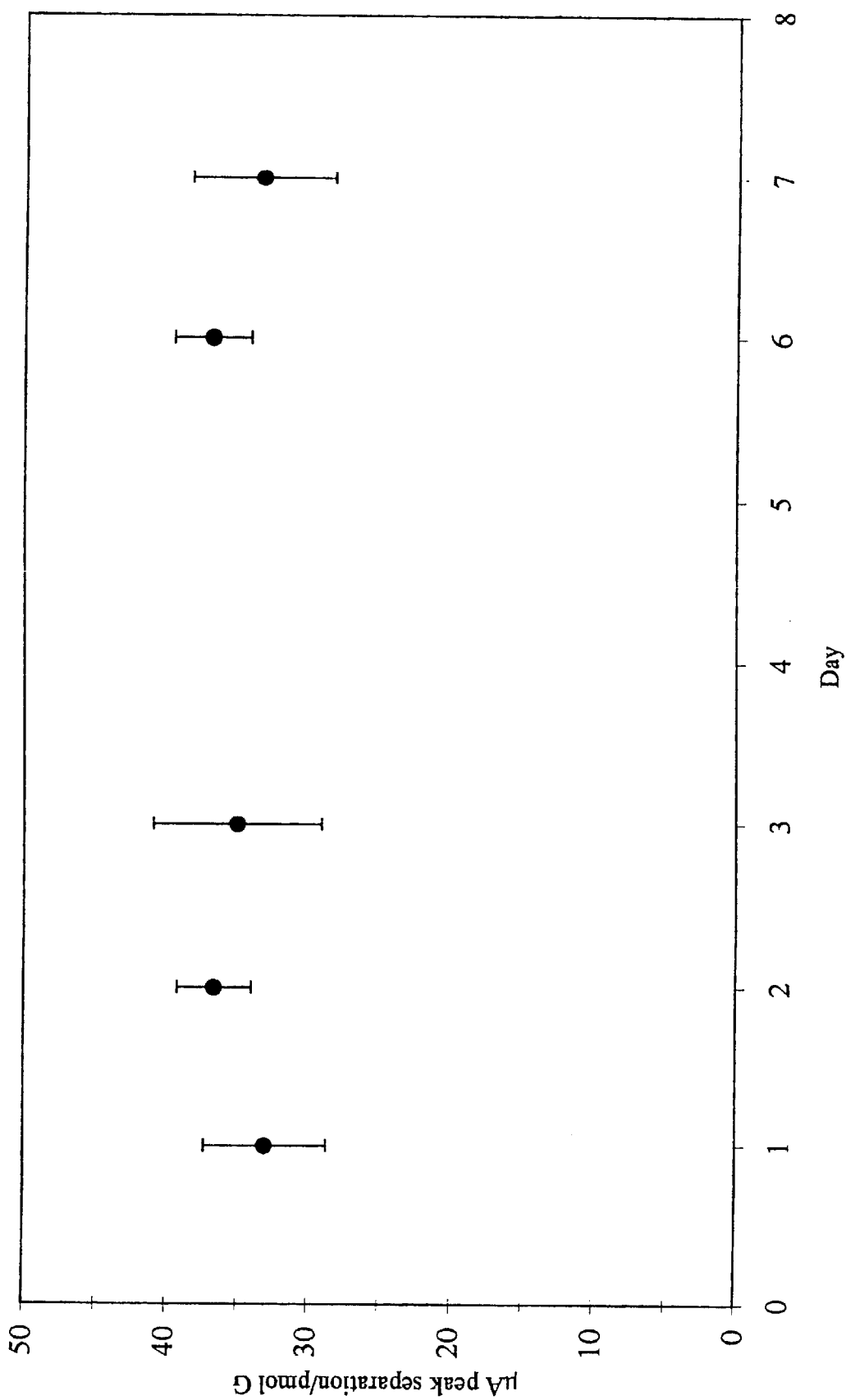
FIG. 3 graphically illustrates the stability of the guanine-containing oligonucleotide monolayer made according to the invention using the 12-carbon carboxy-alkyl phosphonate. Electrochemical measurements were made using cyclic voltammetry at a scan speed of 20 V/s and a $Ru(bpy)_3^{2+}$ concentration of 100 $\mu$M.

The stability of self-assembled monolayers with and without oligonucleotide was evaluated. On Day 0, monolayer was self-assembled on ITO electrodes and guanine-containing oligonucleotide was attached to 60% of the electrodes. All electrodes were then placed in refrigerated storage. On Days 1, 2, 3, 6 and 7, five electrodes (2 with monolayer only and 3 with monolayer plus oligonucleotide) were selected and electrochemically analyzed to determine the signal generated. Electrochemical measurements were made using cyclic voltammetry at 20 V/s and a Ru(bpy)$_3^{2+}$ concentration of 100 μM. The samples were evaluated to determine the μA of signal generated (current) over background per pmole of guanine in the oligonucleotide strand attached to the electrode. Over the seven days, there was no appreciable change in the electrochemical response, and thus, the monolayers were found to be stable over 7 days under these conditions (FIG. 3).

Example 9
Cyclic Voltammogram of Monolayer

Figure 4:
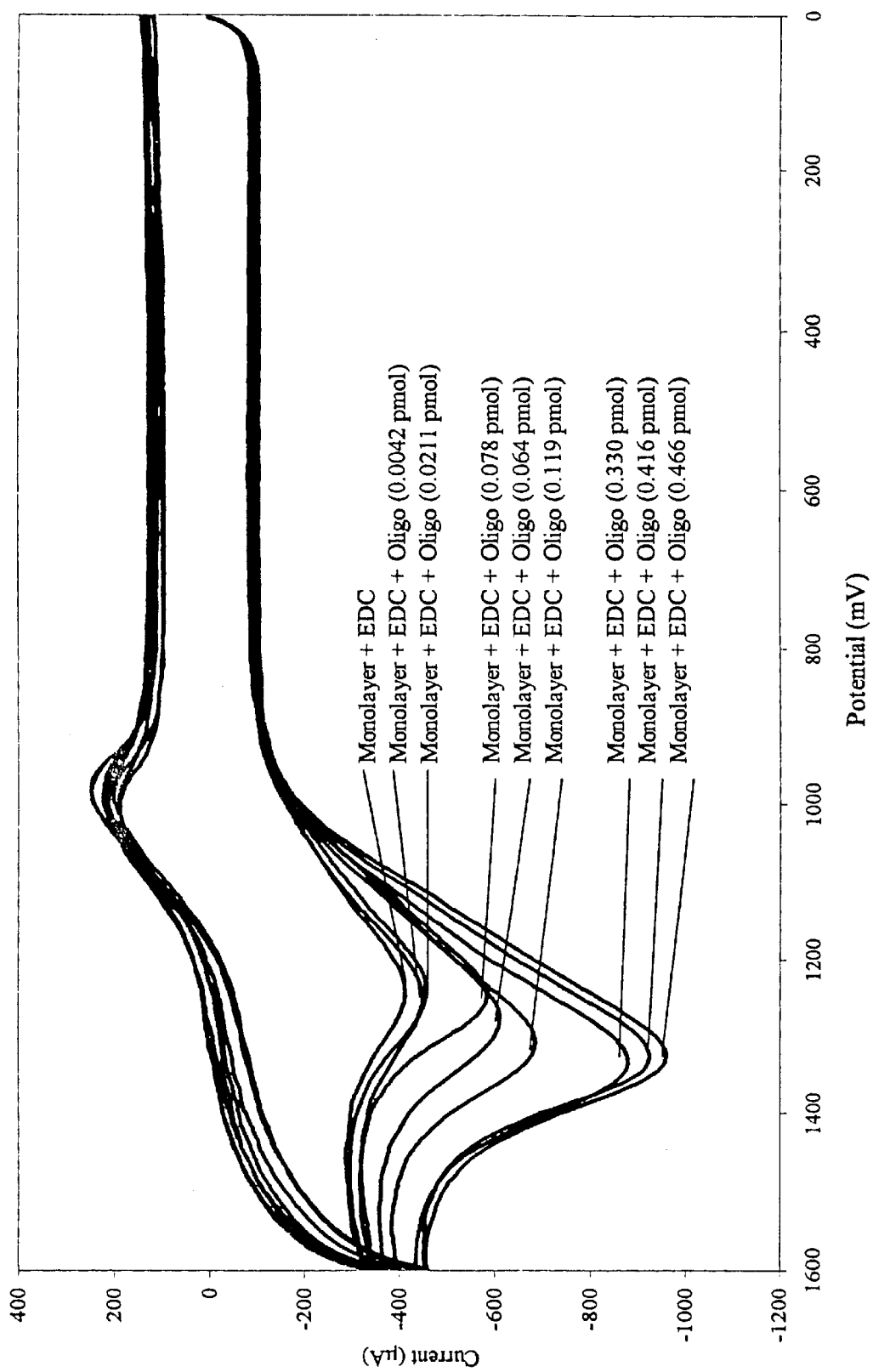
FIG. 4 is a series of cyclic voltammograms illustrating a dose response for oligonucleotide-coupled monolayers that have varying amounts of guanine-containing oligonucleotide attached. Electrochemical measurements were made using cyclic voltammetry at a scan speed of 20 V/s and a $Ru(bpy)_3^{2+}$ concentration of 100 $\mu$M.

FIG. 4 shows the dose response of self-assembled monolayer electrodes with different amounts of guanine-containing oligonucleotide attached. The amount of oligonucleotide coupled to the monolayer ranged from 0.008 to 0.466 picomoles of oligonucleotide strand on each electrode. The oligonucleotide was a synthetic 34-mer with 23 guanines per strand. Electrochemical measurements were made using cyclic voltammetry at 20 V/s and a Ru(bpy)$_3^{2+}$ concentration of 100 μM. This figure shows that one can discriminate between monolayers that have differing amounts of oligonucleotide attached. The signal (current) is proportional to the number of guanines on each electrode.

Figure 5:
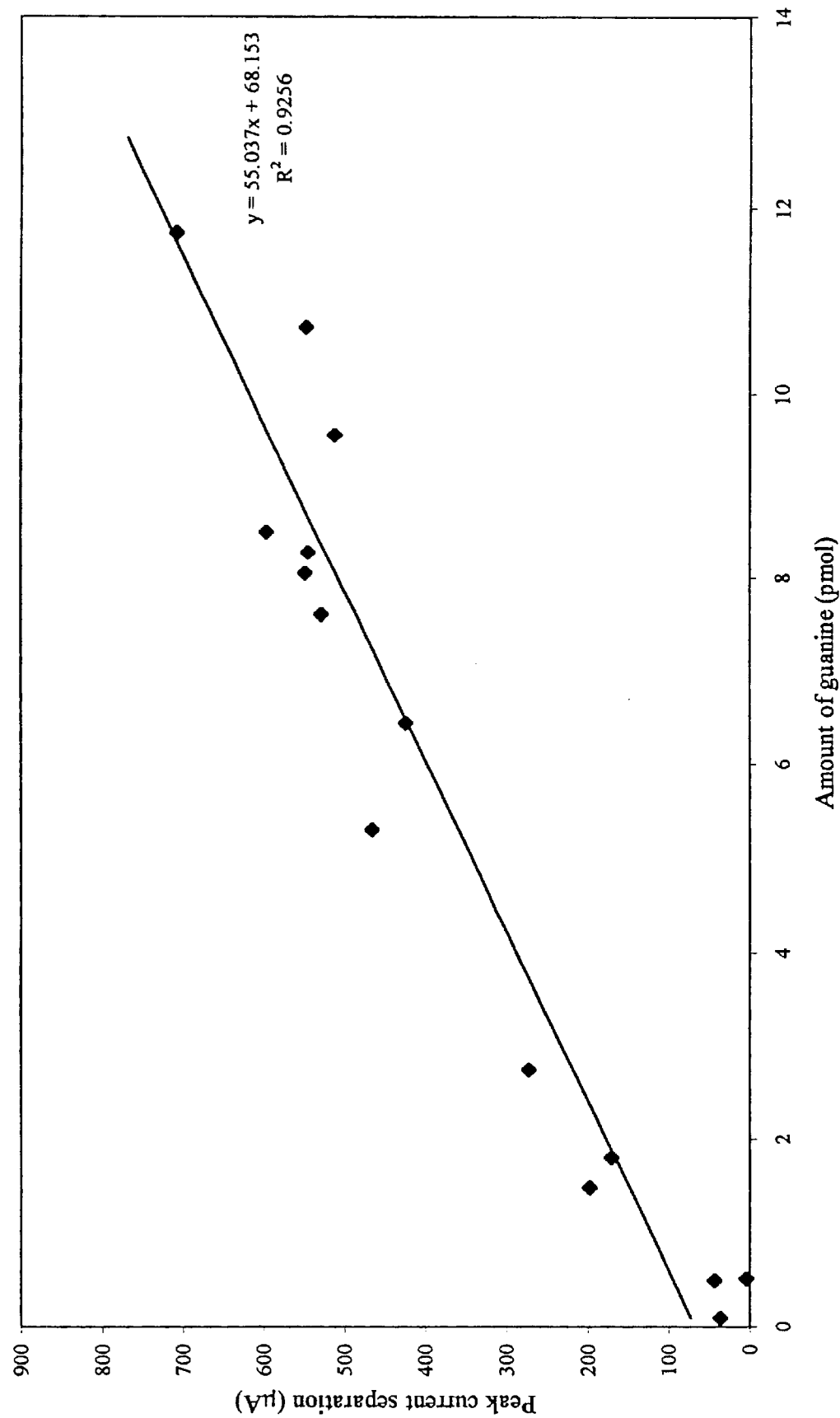
FIG. 5 graphically illustrates the dose response shown in FIG. 4. Electrochemical measurements were made using cyclic voltammetry at a scan speed of 20 V/s and a $Ru(bpy)_3^{2+}$ concentration of 100 $\mu$M.

FIG. 5 is a graphical representation of FIG. 4, where the μA of signal over background vs. pmole of guanine in the oligonucleotide strand on each electrode is plotted. Monolayers were prepared which had varying amounts of oligonucleotide and the electrochemical response (μA of peak separation over background) was measured and plotted as a function of the amount of guanine (in picomoles) in the oligonucleotide coupled to the monolayer. The graph shows the direct correlation between the electrochemical response and the amount of guanine.

Example 10
Alternative Method for Immobilizing Oligonucleotides via Carboxy-alkyl Phosphonates An alternative method of forming self-assembled monolayers with attached oligonucleotides is to couple carboxy-alkyl phosphonate to the oligonucleotide prior to formation of the self-assembled monolayer. An oligonucleotide with an alkyl amine linker on the 3'- or 5'-end is added to a solution of dimethyl sulfoxide containing 0.005–1 mM carboxy-alkyl phosphonate, 0.2 M 1-ethyl-3-(3-dimethylaminopropyl) carbodiimide (EDC) and 0.05 M N-hydroxysuccinimide (NHS). The final volume of the reaction mixture is 100–200 µl and the concentration of the oligonucleotide is 20 µM. The reaction mixture may be incubated for 6–8 hours at 25° C. Radiolabeled oligonucleotide can be used if the degree of oligonucleotide-phosphonate attachment to the electrode is to be quantitated. The reaction mixture (20 µl) containing the carboxy-alkyl phosphonate oligonucleotide conjugate is pipetted onto an ITO glass electrode and incubated for 2–4 hours at 25° C. to allow the monolayer to form. The unattached material is removed and the electrode washed sequentially with water, 0.1 M $NaH_2PO_4$, pH 7.0, 1.0 M NaCl and water.

Generally, this method of coupling the carboxy-alkyl phosphonate to the oligonucleotide yields heterogeneous products that have one or more carboxy-alkyl phosphonate groups attached to the oligonucleotide, the primary attachment site being the alkyl amine on the 3'- or 5'-end of the oligonucleotide, with other exocyclic amines on the bases serving as secondary attachment sites for the carboxy-alkyl phosphonate. Attachment to the ITO electrode and hybridization of target nucleic acid molecules can be impacted by how many carboxy-alkyl phosphonate groups are present on the oligonucleotides.

Other methods may be used to prepare oligonucleotide-phosphonate products using oligonucleotides with blocked exocyclic amino groups so that only one carboxy-alkyl phosphonate is attached to each oligonucleotide via the alkyl amine on the 5'- or 3'-end. For example, a carbodiimide in an aqueous-non-aqueous solvent mixture may be used to couple the carboxy-alkyl phosphonate to the oligonucleotide that is immobilized on glass beads after synthesis and still retains protective groups on the exocyclic amines. After conjugation of the carboxy-alkyl phosphonates, the reactants can be easily washed away to produce a pure product.

The pure carboxy-alkyl phosphonate oligonucleotide conjugate is preferably attached to ITO electrodes by first dissolving the conjugate in 85–100% dimethyl sulfoxide. Free carboxy-alkyl phosphonate is added to the solution to give a solution of alkyl phosphonate having a concentration of about 5 µM–5 mM. This mixture (20 µl) is pipetted onto an ITO glass electrode and incubated for 2–4 hours at 25° C. to allow the monolayer to form. The unattached material is removed, and the electrode washed sequentially with water, 0.1 M sodium phosphate, pH 7.0, 1.0 M NaCl, and water.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. An electrode, comprising:
   (a) a substrate having a conductive working surface thereon; and
   (b) a non-conductive self-assembled monolayer on said conductive working surface, said monolayer comprising phosphonate molecules having at the minimum at least one phosphonate group and at least one $R_1$ group, wherein the $R_1$ group is covalently bound to a member of a binding pair, and through which monolayer a transition metal complex can freely move from reactants immobilized on the monolayer to the conductive working surface to transfer electrons to the conductive working surface; and wherein the conductive working surface comprises an ITO surface.

2. The electrode of claim 1, wherein an organic spacer group, $R_2$, is located between the phosphonate group and the $R_1$ group.

3. The electrode of claim 2, wherein $R_2$ comprises $(CH_2)_{11}$.

4. The electrode of claim 1, wherein the phosphonate molecules comprise a carboxy-alkyl phosphonate.

5. The electrode of claim 4, wherein the carboxy-alkyl phosphonate is 11-carboxyundecane phosphonic acid.

6. The electrode of claim 1, wherein the $R_1$ group was coupled to the member of the binding pair prior to formation of the self-assembled monolayer.

7. The electrode of claim 1, wherein the member of the binding pair comprises an oligonucleotide probe.

8. The electrode of claim 1, wherein the member of the binding pair comprises a protein-binding substance.

9. The electrode of claim 8, wherein the protein-binding substance comprises a protein.

10. The electrode of claim 1, wherein the $R_1$ group has been activated with a coupling agent.

11. The electrode of claim 10, wherein the coupling agent comprises a carbodiimide.

12. The electrode of claim 1, wherein the substrate is selected from the group consisting of metallic substrates and non-metallic substrates.

13. A method of preparing a self-assembled monolayer on an electrode, comprising:
   (a) providing a substrate having a conductive working surface;
   (b) providing phosphonate molecules having at the minimum at least one phosphonate group and at least one $R_1$ group, wherein the $R_1$ group is capable of covalent bonding with a member of a binding pair, wherein said self-assembled monolayer is nonconductive and a transition metal complex can freely move through the monolayer from reactants immobilized on the monolayer to the conductive working surface to transfer electrons to the conductive working surface; and
   (c) contacting the substrate with the phosphonate molecules to form a self-assembled monolayer;
and wherein the conductive working surface comprises an ITO surface.

14. The method of claim 13, wherein an organic spacer group, $R_2$, is located between the phosphonate group and the $R_1$ group.

15. The method of claim 14, wherein $R_2$ comprises $(CH_2)_{11}$.

16. The method of claim 13, wherein the phosphonate molecules comprise a carboxy-alkyl phosphonate.

17. The method of claim 16, wherein the carboxy-alkyl phosphonate is 11-carboxyundecane phosphonic acid.

18. The method of claim 13, wherein the $R_1$ group is coupled to the member of the binding pair prior to formation of the self-assembled monolayer.

19. The method of claim 13, wherein the member of the binding pair comprises an oligonucleotide probe.

20. The method of claim 13, wherein the member of the binding pair comprises a protein-binding substance.

21. The method of claim 20, wherein the protein-binding substance comprises a protein.

22. The method of claim 13, further comprising activating the $R_1$ group with a coupling agent.

23. The method of claim 22, wherein the coupling agent comprises a carbodiimide.

* * * * *

UNITED STATES PATENT AND TRADEMARK OFFICE
CERTIFICATE OF CORRECTION

PATENT NO.   : 6,387,625 B1
DATED        : May 14, 2002
INVENTOR(S)  : Eckhardt et al.

It is certified that error appears in the above-identified patent and that said Letters Patent is hereby corrected as shown below:

<u>Title page,</u>
Item [63], Related U.S. Application Data, should read as follows:

-- Oct. 27, 1998, now Pat. No. 6,132,971, which is a division --

Signed and Sealed this

Fourth Day of January, 2003

JAMES E. ROGAN
*Director of the United States Patent and Trademark Office*